(12) United States Patent
Yuan et al.

(10) Patent No.: US 8,829,039 B2
(45) Date of Patent: Sep. 9, 2014

(54) DIHYDROINDOLINONE DERIVATIVES

(75) Inventors: Zhedong Yuan, Shanghai (CN);
Xiaomin Zhang, Shanghai (CN); Hubo Wang, Shanghai (CN); Xueyan Zhu, Shanghai (CN); Hongjiang Xu, Jiangsu (CN); Hui Fu, Jiangsu (CN); Wei Song, Jiangsu (CN)

(73) Assignees: Shanghai Institute of Pharmaceutical Industry, Shanghai (CN); Jiangsu Chiatai Tianqing Pharmaceutical Co., Ltd., Jiangsu (CN)

( * ) Notice: Subject to any disclaimer, the term of this patent is extended or adjusted under 35 U.S.C. 154(b) by 574 days.

(21) Appl. No.: 12/994,442

(22) PCT Filed: May 25, 2009

(86) PCT No.: PCT/CN2009/071967
§ 371 (c)(1),
(2), (4) Date: Jul. 25, 2011

(87) PCT Pub. No.: WO2009/140928
PCT Pub. Date: Nov. 26, 2009

(65) Prior Publication Data
US 2011/0275671 A1 Nov. 10, 2011

(30) Foreign Application Priority Data
May 23, 2008 (CN) .......................... 2008 1 0098055

(51) Int. Cl.
*A61K 31/33* (2006.01)
*C07D 209/10* (2006.01)
*C07D 403/06* (2006.01)

(52) U.S. Cl.
CPC .................................. *C07D 403/06* (2013.01)
USPC .......................................... 514/414; 548/468

(58) Field of Classification Search
USPC ......................................................... 548/468
See application file for complete search history.

(56) References Cited

U.S. PATENT DOCUMENTS 6,677,368 B2 1/2004 Cui
2007/0191458 A1 8/2007 Hawley et al.

FOREIGN PATENT DOCUMENTS

| CA | 2399358 C | 8/2003 |
|---|---|---|
| CN | 1439005 | 8/2003 |
| CN | 101007801 | 8/2007 |
| CN | 101328166 | 12/2008 |
| WO | WO 01/60814 A2 | 8/2001 |
| WO | WO 02/066463 A1 | 8/2002 |
| WO | WO 2007/085205 A1 | 8/2007 |
| WO | WO 2008/033562 | 3/2008 |
| WO | WO 2008/033743 | 3/2008 |

OTHER PUBLICATIONS

Liang, et al. Document No. 146:379824, (Mar. 29, 2007), retrieved from CAPLUS.*
Liang, et al. Document No. 146:81764, (Dec. 21, 2006), retrieved from CAPLUS.*
Drewes, et al. Document No. 147:378398, (Sep. 20, 2007), retrieved from CAPLUS.*
Rellos, et al. Document No. 146:374831, (Feb. 23, 2007), retrieved from CAPLUS.*
Cancer and Metastasis Reviews (1998), 17(1), 91-106.*
Science (1999), vol. 286, 531-537.*
Cancer [online], [retrieved on Jul 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
idiopathic pulmonary fibrosis [online]. Retrieved from the internet on Jul. 31, 2013. URL; http://www.nlm.nih.gov/medlineplus/ency/article/000069.htm.*
Supplementary European Search Report from EP 09749471, mailed.
Dominguez et al.; "Discovery of N-phenyl nicotinamides as potent inhibitors of Kdr"; Bioorg. Med. Chem. Lett.; 17(21):6003-6008 (2007).
Sun et al.; "Discovery of 5-[5-Fluoro-2-oxo-1,2-dihydroindol-(3Z)-ylidenemthyl]-2,4-dimethyl-1H-pyrrole-3-carboxylic Acid (2-Diethylaminoethyl)amide, a Novel Tyrosine Kinase Inhibitor Targeting Vascular Endothelial and Platelet-Derived Growth Factor Receptor Tyrosine Kinase"; J. Med. Chem.; 46:1116-119 (2003).
International Search Report dated Aug. 27, 2009, issued in related International Application No. PCT/CN2009/071967, filed May 25, 2009.
Office Action from Russian Application No. 2010152560 dated Feb. 13, 2012.
Office Action from Canadian Application No. 2,725,001 dated Jan. 15, 2013.
Office Action from Canadian Application No. 2,725,001 dated May 14, 2012.

* cited by examiner

*Primary Examiner* — Shawquia Young
(74) *Attorney, Agent, or Firm* — Kilpatrick Townsend & Stockton LLP

(57) ABSTRACT

Disclosed are dihydroindolone compounds which can modulate the activity of protein tyrosine kinases, a method for preparing the same, and pharmaceutical compositions comprising the same. Also disclosed are use of such compounds and pharmaceutical compositions thereof in the treatment and/or prophylaxis of protein tyrosine kinase associated diseases in an organism, particularly in the treatment and/or prophylaxis of tumors and fibroblast proliferation associated diseases.

13 Claims, 1 Drawing Sheet

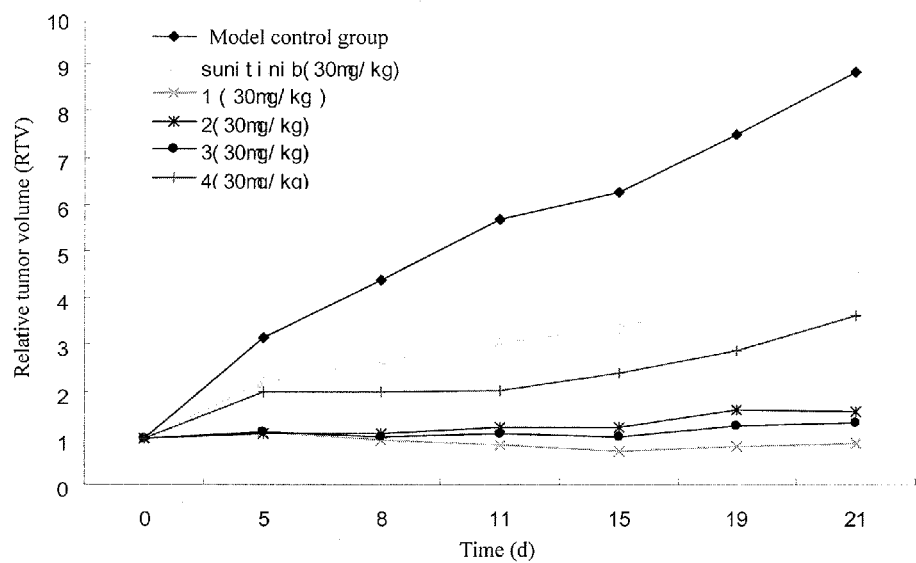

DIHYDROINDOLINONE DERIVATIVES

This application is the U.S. National Stage entry of International Application No. PCT/CN2009/071967, filed May 25, 2009, which claims priority to Chinese Application No. 200810098055.5, filed May 23, 2008, the contents of which are herein incorporated by reference in their entirety.

FIELD OF THE INVENTION

The present invention relates to heterocyclic compounds which can regulate the activity of protein tyrosine kinases ("PTKs"), methods for preparing the compounds, pharmaceutical compositions comprising the compounds, and use of the compounds and pharmaceutical compositions thereof in the treatment and/or prophylaxis of protein tyrosine kinase associated diseases in organisms, particularly in the treatment and/or prophylaxis of tumors and fibroblast proliferation associated diseases.

BACKGROUND OF THE INVENTION

Protein tyrosine kinases (PTKs) are kinases that catalyze the transfer of γ-phosphates on adenosine triphosphates (ATPs) to tyrosine residues of proteins. It is known that the protein tyrosine kinase (PTK) signaling pathways play an important role in growth, proliferation, differentiation, metabolism and apoptosis of cells.

PTKs include a receptor type and a non-receptor type. Receptor type PTKs include nine sub-types based on their structures, of which an epidermal growth factor receptor (EGFR) family, a vascular endothelial growth factor receptor (VEGFR) family, a platelet-derived growth factor receptor (PDGFR) family, a fibroblast growth factor receptor (FGFR) family and an insulin receptor (INSR) family are common. Non-receptor type PTKs are completely intracellular PTKs, also known as "cell tyrosine kinases", of which a steroid receptor coactivator (SRC) family is common.

Interactions between growth factors and their receptors are necessary for the normal regulation of cell growth. However, under certain conditions, due to mutation or over-expression, inappropriate or uncontrolled activation of these receptors, i.e., aberrant protein tyrosine kinase activity may result in uncontrolled cell growth, which may cause tumor growth. For example, members of the EGFR family are particularly important growth factor receptor tyrosine kinases associated with epidermal cell tumorigenesis. EGFR are overexpressed in many kinds of epidermal tumor cells. A VEGFR family is also a factor associated with cell tumorigenesis.

Overexpressed or mutated protein tyrosine kinases are associated with cancers. Consequently, inhibiting protein tyrosine kinases will be of significance in treating cancers.

Currently, various small molecule tyrosine kinase inhibitors, such as GLEEVEC, TARCEVA, IRESSA, SUNITINIB and the like, have been used successfully in clinical treatments as anti tumor drugs.

Besides tumors, tissue and organ fibrosis is another disease seriously endangering human health. Fibrosis refers to the excessive deposition of fibrous connective tissues and the like, which results from imbalance between proliferation and degradation of fibrous tissues. One common feature of such diseases is over proliferation of fibroblasts. Currently, tissue and organ fibrosis commonly include pulmonary fibrosis, hepatic fibrosis, chronic pancreatitis, scleroderma, renal glomerular fibrosis, and multiple organ fibrosis supervened with radiochemotherapy and tissue transplantation, etc.

Previous studies have shown that FGFRs play a role in binding fibroblast growth factors and transferring signals thereof. This kind of signal transduction is associated with proliferation and differentiation of various types of cells. Excessive autocrine of fibroblast growth factors results in many diseases. Furthermore, abnormal signal transduction mediated by FGFRs is closely associated with fibrosis diseases.

Aberrant protein tyrosine kinase activity is also implicated in a variety of other disorders, such as inflammation, immune diseases, cardiovascular diseases, asthma, and nervous system diseases. Although numerous small molecular tyrosine kinase inhibitors have been developed for treatment and prophylaxis of various protein tyrosine kinases associated diseases, a need for new tyrosine kinase inhibitors for the treatment and/or prophylaxis of protein tyrosine kinases associated diseases, particularly for the treatment and/or prophylaxis of tumors and fibroblast proliferation associated diseases, still exists.

SUMMARY OF THE INVENTION

In one aspect, the present invention relates to a compound of formula I, or a salt thereof, preferably a pharmaceutically acceptable salt thereof:

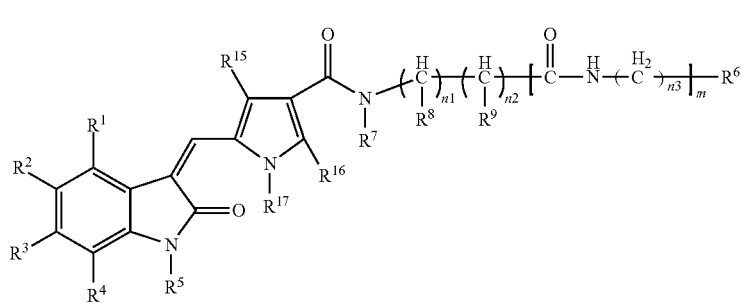

Formula I wherein $R^1$, $R^2$, $R^3$ and $R^4$ are each independently selected from the group consisting of hydrogen, halogen, optionally substituted alkyl, hydroxy, optionally substituted alkoxy, optionally substituted cycloalkoxy, optionally substituted aryl, cyano, amino, optionally substituted monoalkyl amino and optionally substituted dialkyl amino;

$R^5$, $R^7$ and $R^{17}$ are each independently selected from the group consisting of hydrogen and optionally substituted alkyl;

$R^6$ is selected from the group consisting of amino, optionally substituted monoalkyl amino, optionally substituted dialkyl amino, optionally substituted aryl, optionally substituted heteroaryl and optionally substituted heterocycloalkyl, with the proviso that when $R^6$ is heteroaryl or heterocycloalkyl, the heteroatom in $R^6$ is not connected to other groups in formula I directly;

$R^8$ and $R^9$ may be the same or different, and are each independently selected from the group consisting of hydrogen, optionally substituted alkyl, hydroxy, optionally substituted alkoxy, optionally substituted cycloalkoxy, optionally substituted aryl, optionally substituted aryloxy and optionally substituted aralkyl;

$R^{15}$ and $R^{16}$ may be the same or different, and are each independently selected from the group consisting of hydrogen, optionally substituted alkyl, amino, optionally substituted monoalkyl amino, optionally substituted dialkyl amino and optionally substituted aryl;

n1, n2 and n3 are each independently an integer from 0 to 4;

m is an integer from 0 to 2.

In another aspect of the invention, a compound of formula I or a salt thereof is preferably a compound of formula II, or a salt thereof, preferably a pharmaceutically acceptable salt thereof:

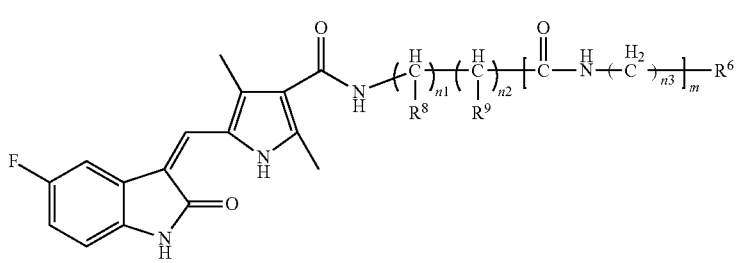

Formula II wherein, $R^6$, $R^8$, $R^9$, n1, n2, and n3 and m have the same meanings as defined in formula I.

Another aspect of the invention relates to a pharmaceutical composition, comprising at least one compound of formula I or a salt thereof, or a compound of formula II or a salt thereof as defined above and at least one pharmaceutically acceptable carrier, adjuvant and/or medium.

Another aspect of the invention relates to a method for preparing the compound of formula I or salt thereof as defined above, comprising reacting a corresponding dihydroindolone intermediate of formula III with an intermediate of formula IV in the presence of an alkali:

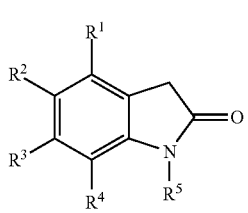

Formula III wherein, $R^1$~$R^5$ have the same meanings as defined in formula I,

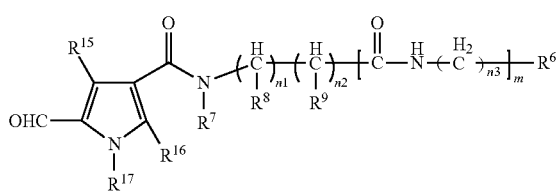

Formula IV wherein, $R^6$~$R^9$, $R^{15}$~$R^{17}$ and n1~n3 and m have the same meanings as defined in formula I.

Another aspect of the invention relates to a method for preparing the compound of formula II or salt thereof as defined above, comprising reacting a corresponding 5-fluoro-2-indolone compound of formula V with an intermediate of formula VI in the presence of an alkali:

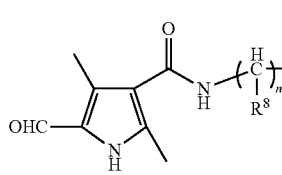

Formula V

Formula VI wherein $R^6$, $R^8$, $R^9$, n1~n3 and m have the same meanings as defined in formula I.

Another aspect of the invention relates to use of compounds of formula I or salts thereof, or pharmaceutical compositions thereof, or compounds of formula II or salts thereof or pharmaceutical compositions thereof as defined above in the preparation of medicaments for the treatment and/or prophylaxis of tyrosine kinases associated diseases.

Another aspect of the invention relates to use of compounds of formula I or salts thereof or pharmaceutical compositions thereof, or compounds of formula II or salts thereof or pharmaceutical compositions thereof as defined above in the preparation of medicaments for the treatment and/or prophylaxis of tumors.

Another aspect of the invention relates to use of compounds of formula I or salts thereof or pharmaceutical compositions thereof, or compounds of formula II or salts thereof or pharmaceutical compositions thereof as defined above in the preparation of medicaments for the treatment and/or prophylaxis of fibroblast proliferation associated diseases.

Another aspect of the invention relates to a method of treating and/or preventing tyrosine kinases associated diseases, comprising administering to a subject in need thereof a therapeutically effective amount of at least one compound of formula I or a salt thereof or a pharmaceutical composition thereof, or at least one compound of formula II or a salt thereof or a pharmaceutical composition thereof, as defined above.

Another aspect of the invention relates to a method of treating and/or preventing tumors, comprising administering to a subject in need thereof a therapeutically effective amount of at least one compound of formula I or a salt thereof or a pharmaceutical composition thereof, or at least one compound of formula II or a salt thereof or a pharmaceutical composition thereof, as defined above.

Another aspect of the invention relates to a method of treating and/or preventing fibroblast proliferation associated diseases, comprising administering to a subject in need thereof a therapeutically effective amount of at least one compound of formula I or a salt thereof or a pharmaceutical composition thereof, or at least one compound of formula II or a salt thereof or a pharmaceutical composition thereof, as defined above.

BRIEF DESCRIPTION OF THE DRAWINGS

The drawings are incorporated in and form a part of the Specification only to illustrate some preferred embodiments of the invention. The drawings, together with other parts of the Specification, serve to explain some preferred embodiments of the invention to those skilled in the art.

FIG. 1 shows the growth inhibition of HT-29 human colon tumor in nude mice by compounds 1-4 of the invention and Sunitinib.

DETAILED DESCRIPTION OF THE INVENTION

In the above definitions of compounds of formula (I) and the following embodiments, the terms used have the following meanings:

The term "halogen" refers to fluorine, chlorine, bromine or iodine, preferably fluorine or chlorine, more preferably fluorine.

The term "hydroxyl" refers to —OH group.

The term "cyano" refers to —CN group.

The term "alkyl" refers to a straight or branched, substituted or unsubstituted saturated aliphatic hydrocarbon group consisting of carbon atoms and hydrogen atoms, attached to other parts of the molecule through a single bond. The alkyl contains 1-8 carbon atoms, preferably 1-4 carbon atoms. Examples of the unsubstituted alkyl include, but are not limited to, methyl, ethyl, propyl, 2-propyl, n-butyl, isobutyl, tert-butyl, n-pentyl, 2-methylbutyl, neopentyl, n-hexyl, 2-methylhexyl, etc.

The term "alkoxy" refers to —OR$_a$ group, wherein R$_a$ represents a substituted or unsubstituted alkyl containing 1-8 carbon atoms, preferably 1-4 carbon atoms as defined above. Examples of the unsubstituted alkoxy include, but are not limited to, methoxy, ethoxy, propoxy, isopropoxy, n-butoxy, isobutoxy, tert-butoxy, n-pentoxy, 2-methylbutoxy, neopentoxy, n-hexoxy, 2-methylhexoxy, etc.

The term "cycloalkoxy" refers to —OR$_b$ group, wherein R$_b$ represents a substituted or unsubstituted saturated non-aromatic monocyclic hydrocarbon group, consisting of carbon atoms and hydrogen atoms, having 3-8 carbon atoms, preferably 3-6 carbon atoms. Examples of the unsubstituted cycloalkoxy include, but are not limited to, cyclopropoxy, cyclobutoxy, cyclopentoxy, cyclohexoxy, cycloheptoxy, cyclooctoxy, etc.

The term "amino" refers to —NH$_2$ group.

The term "monoalkyl amino" refers to —NH(alkyl), wherein the alkyl represents a substituted or unsubstituted alkyl containing 1-8 carbon atoms, preferably 1-4 carbon atoms as defined above.

The term "dialkyl amino" refers to —N(alkyl)$_2$, wherein the alkyl represents a substituted or unsubstituted alkyl containing 1-8 carbon atoms, preferably 1-4 carbon atoms as defined above, and the two alkyls may be the same or different.

The term "aryl" refers to a substituted or unsubstituted, all-carbon monocyclic or condensed polycyclic aromatic cyclic group, with a fully conjugated π electric system, and containing 6-14 carbon atoms, preferably 6-12 carbon atoms, most preferably 6 carbon atoms. Examples of the unsubstituted aryl include, but are not limited to, phenyl, naphthyl and anthryl.

The term "aryloxy" refers to —OR$_c$ group, wherein R$_c$ represents a substituted or unsubstituted aryl as defined above. Examples of the unsubstituted aryloxy include, but are not limited to, phenoxy, naphthoxy, etc.

The term "aralkyl" refers to an unsubstituted alkyl, preferably an unsubstituted $C_1$-$C_4$ alkyl as defined above, substituted with a substituted or unsubstituted aryl as defined above. Examples of the unsubstituted aralkyl include, but are not limited to, —CH$_2$-phenyl, —(CH$_2$)$_2$-phenyl, —(CH$_2$)$_3$-phenyl, —CH$_2$—CH(CH$_3$)-phenyl, —(CH$_2$)$_4$-phenyl, —CH$_2$—CH(CH$_3$)—CH$_2$-phenyl, —CH$_2$—CH$_2$—CH(CH$_3$)-phenyl, etc.

The term "heteroaryl" refers to a substituted or unsubstituted 5- or 6-membered aromatic cyclic group, containing hydrogen atoms, 3-5 carbon atoms, and 1-2 heteroatoms selected from nitrogen, oxygen and sulphur atoms. Preferably, the heteroaryl represents 5-membered aromatic cyclic group. Examples of the unsubstituted heteroaryl include, but are not limited to, pyrrole, furan, thiophene, imidazole, oxazole, pyrazole, pyridine, and pyrimidine.

The term "heterocycloalkyl" refers to a substituted or unsubstituted 5- to 10-membered single ring or fused ring non-aromatic cyclic group, consisting of 3-9 carbon atoms and 1-2 heteroatoms selected from nitrogen, oxygen and sulphur atoms. Examples of the unsubstituted heterocycloalkyl include pyrrolidinyl, piperidyl, piperazinyl, morpholinyl, etc.

The term "optional" or "optionally" means that the event or condition described subsequently may happen or not. And, the description includes both the situation that the event or condition happens and the situation that the event or condition does not happen. For example, "optionally substituted aryl" means that the aryl may be substituted or not be substituted, and the description comprises substituted and unsubstituted aryl.

When a substituent is defined as "optionally substituted", unless otherwise expressly stated in the Specification, it means that the substituent can be substituted with one or more groups each independently selected from the group consisting of alkyl, alkenyl, alkynyl, alkoxy, alkenoxy, alkynoxy, cycloalkyl, cycloalkenyl, cycloalkoxy, cycloalkenoxy, halogen, haloalkyl, haloalkenyl, haloalkoxy, hydroxyl, sulfydryl, nitro, cyano, acyl, carboxyl, acyloxy, acylamino, carboxylalkyl, amino, monoalkyl amino, dialkyl amino, aryl, aryloxy, aralkyl, aralkenyl, heterocycloalkyl, heterocycloalkyl alkyl, heteroaryl, or heteroaryl alkyl.

In some embodiments, the alkyl, alkoxy, cycloalkoxy, monoalkyl amino and dialkyl amino are each independently unsubstituted or substituted with one or more substituents selected from halogen, hydroxyl and sulfydryl. In some embodiments, the aryl, aryloxy, aralkyl, heteroaryl, heterocycloalkyl are each independently unsubstituted or substituted with one or more substituents selected from alkyl, aryl, aralkyl, amino, monoalkyl amino, dialkyl amino, halogen, hydroxyl and sulfydryl.

The term "therapeutically effective amount" refers to the amount of the compounds of the invention sufficient to effectively treat tyrosine kinases associated diseases (particularly tumors and fibroblast proliferation associated diseases), when administered to mammals, preferably human beings, suffering from the above diseases. The amount of the compounds of the invention constituting so-called "therapeutically effective amount" depends on the compound, disease condition and severity thereof, the way of administration and age of the mammal to be treated, but can be routinely determined by those skilled in the art on the basis of their knowledge and the disclosure herein.

The term "treatment" or "treating" refers to the administration of the compounds or preparations of the invention for preventing, ameliorating or eliminating diseases or one or more symptoms associated with the diseases, comprising:

(i) prophylaxis of occurrence of diseases or conditions in mammals, particularly when the mammals are susceptible to the conditions, but have not been diagnosed with them;

(ii) inhibition of diseases or conditions, i.e. restraining their development; or (iii) relief of diseases or conditions, i.e. recovering from the diseases or conditions.

According to the first aspect, the invention relates to a compound of formula I, or a salt thereof, preferably a pharmaceutically acceptable salt:

with the proviso that when $R^6$ is heteroaryl or heterocycloalkyl, the heteroatom in $R^6$ is not connected to other groups in formula I directly.

$R^8$ and $R^9$ may be the same or different, and are each independently selected from the group consisting of hydrogen, optionally substituted alkyl, hydroxy, optionally substituted alkoxy, optionally substituted cycloalkoxy, optionally substituted aryl, optionally substituted aryloxy and optionally substituted aralkyl.

$R^{15}$ and $R^{16}$ may be the same or different, and are each independently selected from the group consisting of hydrogen, optionally substituted alkyl, amino, optionally substituted monoalkyl amino, optionally substituted dialkyl amino and optionally substituted aryl.

n1, n2 and n3 are each independently an integer from 0 to 4.

m is an integer from 0 to 2.

In some embodiments, the optionally substituted aryl, optionally substituted heteroaryl and optionally substituted heterocycloalkyl in $R^6$ are each independently unsubstituted or substituted with one or more substituents selected from the group consisting of alkyl, aralkyl, amino, monoalkyl amino and dialkyl amino.

In some embodiments, $R^1$, $R^3$ and $R^4$ are each independently selected from the group consisting of hydrogen, $C_1$-$C_4$ alkyl, $C_1$-$C_4$ alkoxy and aryl. In some other embodiments, $R^1$, $R^3$ and $R^4$ are selected from the group consisting of hydrogen and $C_1$-$C_4$ alkyl. In some other embodiments, $R^1$, $R^3$ and $R^4$ are each independently hydrogen.

In some embodiments, $R^2$ is hydrogen, $C_1$-$C_4$ alkyl, halogen or cyano. In some other embodiments, $R^2$ is halogen. In some other embodiments, $R^2$ is fluorin.

In some embodiments, $R^5$ is selected from the group consisting of hydrogen and $C_1$-$C_4$ alkyl. In some other embodiments, $R^5$ is selected from the group consisting of hydrogen and methyl. In some other embodiments, $R^5$ is hydrogen.

In some embodiments, $R^6$ is selected from the group consisting of amino, monoalkyl amino, dialkyl amino, and aryl

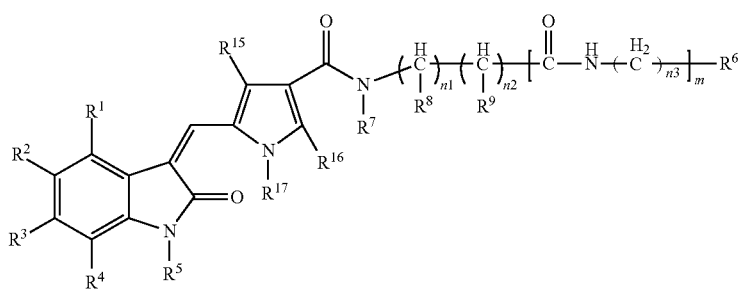

Formula I $R^1$, $R^2$, $R^3$ and $R^4$ are each independently selected from the group consisting of hydrogen, halogen, optionally substituted alkyl, hydroxy, optionally substituted alkoxy, optionally substituted cycloalkoxy, optionally substituted aryl, cyano, amino, optionally substituted monoalkyl amino and optionally substituted dialkyl amino.

$R^5$, $R^7$ and $R^{17}$ are each independently selected from the group consisting of hydrogen and optionally substituted alkyl.

$R^6$ is selected from the group consisting of amino, optionally substituted monoalkyl amino, optionally substituted dialkyl amino, optionally substituted aryl, optionally substituted heteroaryl and optionally substituted heterocycloalkyl, and heterocycloalkyl unsubstituted or substituted with a substituent selected from the group consisting of $C_1$-$C_4$ alkyl, aralkyl, amino, monoalkyl amino and dialkyl amino. In some other embodiments, $R^6$ is selected from the group consisting of amino, monoalkyl amino, dialkyl amino, and phenyl and 5- or 6-membered heterocycloalkyl unsubstituted or substituted with a substituent selected from the group consisting of $C_1$-$C_4$ alkyl, aralkyl, amino, monoalkyl amino and dialkyl amino. In some other embodiments, $R^6$ is selected from the group consisting of piperidin-2-yl, piperidin-4-yl, and pyrrolidin-3-yl and pyrrolidin-2-yl unsubstituted or substituted with $C_1$-$C_4$ alkyl or aralkyl, amino, monoalkyl amino, dialkyl amino, and phenyl substituted with di$C_1$-$C_4$ alkylamino.

In some embodiments, $R^7$ is hydrogen or $C_1$-$C_4$ alkyl. In some other embodiments, $R^7$ is hydrogen or methyl. In some other embodiments, $R^7$ is hydrogen.

In some embodiments, $R^8$ and $R^9$ are selected from hydrogen, $C_1$-$C_4$ alkyl, hydroxy, or $C_1$-$C_4$ alkoxy. In some other embodiments, $R^8$ and $R^9$ are selected from hydrogen or $C_1$-$C_4$ alkyl. In some other embodiments, $R^8$ and $R^9$ are selected from hydrogen or methyl.

In some embodiments, $R^{15}$ and $R^{16}$ are each independently selected from the group consisting of hydrogen and $C_1$-$C_4$ alkyl. In some other embodiments, $R^{15}$ and $R^{16}$ are each independently $C_1$-$C_4$ alkyl. In some other embodiments, $R^{15}$ and $R^{16}$ are each independently methyl.

In some embodiments, $R^{17}$ is selected from the group consisting of hydrogen and $C_1$-$C_4$ alkyl. In some other embodiments, $R^{17}$ is selected from the group consisting of hydrogen and methyl. In some other embodiments, $R^{17}$ is hydrogen.

In some embodiments, n1, n2 and n3 are each independently selected from 0, 1 or 2.

In some embodiments, m is selected from 0 or 1.

In some embodiments, $R^1$, $R^3$ and $R^4$ are each independently selected from the group consisting of hydrogen, $C_1$-$C_4$ alkyl, $C_1$-$C_4$ alkoxy and aryl, $R^2$ is selected from the group consisting of hydrogen, $C_1$-$C_4$ alkyl, halogen and cyano, $R^5$, $R^7$, $R^{15}$, $R^{16}$ and $R^{17}$ are each independently selected from the group consisting of hydrogen and $C_1$-$C_4$ alkyl, $R^6$ is selected from the group consisting of amino, monoalkyl amino, dialkyl amino, and aryl and heterocycloalkyl unsubstituted or substituted with a substituent selected from the group consisting of $C_1$-$C_4$ alkyl, aralkyl, amino, monoalkyl amino and dialkyl amino, and $R^8$ and $R^9$ are each independently selected from the group consisting of hydrogen, $C_1$-$C_4$ alkyl, hydroxy and $C_1$-$C_4$ alkoxy.

In some other embodiments, $R^1$, $R^3$ and $R^4$ are each independently selected from the group consisting of hydrogen and $C_1$-$C_4$ alkyl, $R^2$ is halogen, $R^5$, $R^7$ and $R^{17}$ are each independently selected from hydrogen and methyl, $R^6$ is selected from the group consisting of amino, monoalkyl amino, dialkyl amino, and phenyl and 5- or 6-membered heterocycloalkyl unsubstituted or substituted with a substituent selected from the group consisting of $C_1$-$C_4$ alkyl, aralkyl, amino, monoalkyl amino and dialkyl amino, $R^8$ and $R^9$ are each independently selected from the group consisting of hydrogen and $C_1$-$C_4$ alkyl, and $R^{15}$ and $R^{16}$ are each independently $C_1$-$C_4$ alkyl.

In some other embodiments, $R^1$, $R^3$ and $R^4$ are each independently hydrogen, $R^2$ is fluorine, $R^5$, $R^7$ and $R^{17}$ are each independently selected from the group consisting of hydrogen, $R^6$ is selected from the group consisting of piperidin-2-yl, piperidin-4-yl, and pyrrolidin-3-yl and pyrrolidin-2-yl unsubstituted or substituted with $C_1$-$C_4$ alkyl or aralkyl, and amino, monoalkyl amino, dialkyl amino, and phenyl substituted with $diC_1$-$C_4$ alkylamino, $R^8$ and $R^9$ are each independently selected from the group consisting of hydrogen and methyl, and $R^{15}$ and $R^{16}$ are each independently methyl.

In some embodiments, a compound of formula I or a salt thereof is preferably a compound of formula II, or a salt thereof, preferably a pharmaceutically acceptable salt thereof:

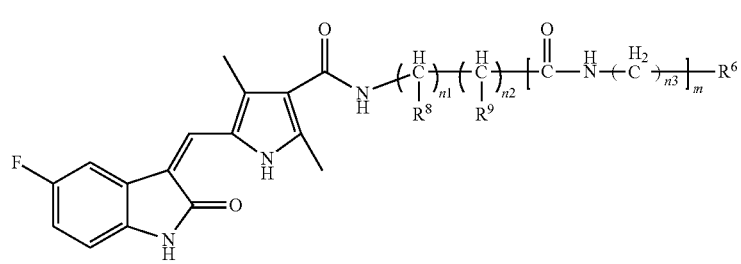

Formula II wherein, $R^6$, $R^8$, $R^9$, n1, n2, n3 and m have the same meanings as defined in formula I.

In some embodiments, $R^6$ is selected from the group consisting of amino, monoalkyl amino, dialkyl amino, and aryl and heterocycloalkyl unsubstituted or substituted with a substituent selected from the group consisting of $C_1$-$C_4$ alkyl, aralkyl, amino, monoalkyl amino and dialkyl amino. In some other embodiments, $R^6$ is selected from the group consisting of amino, monoalkyl amino, dialkyl amino, and phenyl and 5- or 6-membered heterocycloalkyl unsubstituted or substituted with a substituent selected from the group consisting of $C_1$-$C_4$ alkyl, aralkyl, amino, monoalkyl amino and dialkyl amino. In some other embodiments, $R^6$ is selected from the group consisting of piperidin-2-yl, piperidin-4-yl, and pyrrolidin-3-yl and pyrrolidin-2-yl unsubstituted or substituted with $C_1$-$C_4$ alkyl or aralkyl, and amino, monoalkyl amino, dialkyl amino, and phenyl substituted with $diC_1$-$C_4$ alkylamino.

In some embodiments, $R^8$ and $R^9$ are each independently selected from the group consisting of hydrogen, $C_1$-$C_4$ alkyl, hydroxy and $C_1$-$C_4$ alkoxy. In some other embodiments, $R^8$ and $R^9$ are each independently selected from the group consisting of hydrogen and $C_1$-$C_4$ alkyl. In some other embodiments, $R^8$ and $R^9$ are each independently selected from the group consisting of hydrogen and methyl.

In some embodiments, n1, n2 and n3 are each independently selected from 0, 1 or 2.

In some embodiments, m is selected from 0 or 1.

In some embodiments, the compounds of formula II or salts thereof are preferably the following compounds or salts thereof: $R^8$ and $R^9$ are each independently selected from the group consisting of hydrogen and $C_1$-$C_4$ alkyl, $R^6$ is selected from the group consisting of amino, monoalkyl amino, dialkyl amino, and heterocycloalkyl and aryl unsubstituted or substituted with a substituent selected from the group consisting of $C_1$-$C_4$ alkyl, aralkyl, amino, monoalkyl amino and dialkyl amino, n1, n2 and n3 are each independently an integer from 0 to 2, and m is 0 or 1.

In some embodiments, more preferably, the compounds of formula II or salts thereof are the following compounds or salts thereof: $R^8$ and $R^9$ are each independently selected from the group consisting of hydrogen and $C_1$-$C_4$ alkyl, $R^6$ is selected from the group consisting of amino, monoalkyl amino, dialkyl amino, and phenyl and 5- or 6-membered heterocycloalkyl unsubstituted or substituted with a substituent selected from the group consisting of $C_1$-$C_4$ alkyl, aralkyl, amino, monoalkyl amino and dialkyl amino, n1, n2 and n3 are each independently an integer from 0 to 2, and m is 0 or 1.

In some embodiments, especially preferably, the compounds of formula II or salts thereof are the following compounds or salts thereof: $R^8$ and $R^9$ are each independently selected from the group consisting of hydrogen and methyl, $R^6$ is selected from the group consisting of piperidin-2-yl, piperidin-4-yl, and pyrrolidin-3-yl and pyrrolidin-2-yl unsubstituted or substituted with $C_1$-$C_4$ alkyl or aralkyl, and phenyl substituted with $diC_1$-$C_4$ alkylamino, and $diC_1$-$C_4$ alkylamino, n1, n2 and n3 are each independently an integer from 0 to 2, and m is 0 or 1.

Preferred compounds of formula I and salts thereof are illustrated as follows, but are not limited thereto:

| No. | Structure | Name |
|---|---|---|
| 1 | 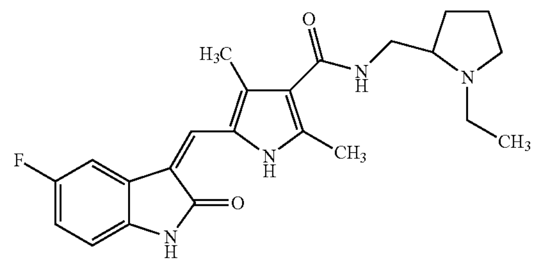 [SMILES: CCN1CCCC1CNC(=O)c1c(C)[nH]c(/C=C2\C(=O)Nc3ccc(F)cc32)c1C] | N-[(1-ethylpyrrolidin-2-yl)methyl]-5-(5-fluoro-2-oxo-1,2-dihydroindole-3-methylene)-2,4-dimethyl-1H-pyrrole-3-formamide |
| 2 | 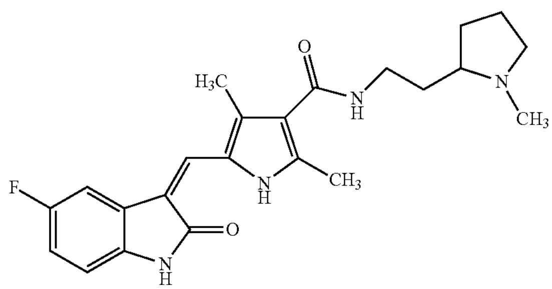 [SMILES: Cc1[nH]c(/C=C2\C(=O)Nc3ccc(F)cc32)c(C)c1C(=O)NCCC1CCCN1C] | N-[(1-methylpyrrolidin-2-yl)ethyl]-5-(5-fluoro-2-oxo-1,2-dihydroindole-3-methylene)-2,4-dimethyl-1H-pyrrole-3-formamide |
| 3 | 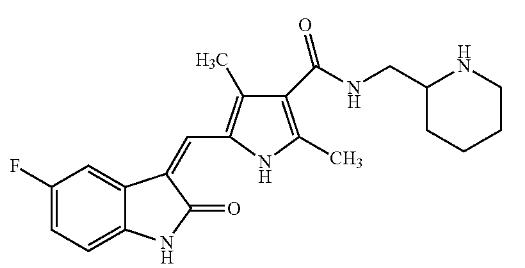 [SMILES: Cc1[nH]c(/C=C2\C(=O)Nc3ccc(F)cc32)c(C)c1C(=O)NCC1CCCCN1] | N-[(piperidin-2-yl)methyl-5-(5-fluoro-2-oxo-1,2-dihydroindole-3-methylene)-2,4-dimethyl-1H-pyrrole-3-formamide |
| 4 | 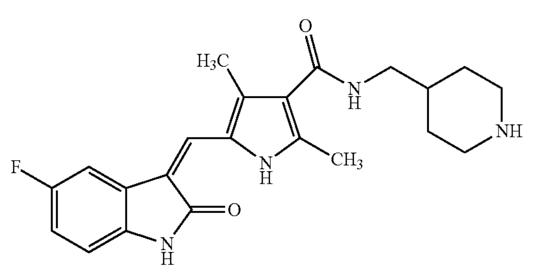 [SMILES: Cc1[nH]c(/C=C2\C(=O)Nc3ccc(F)cc32)c(C)c1C(=O)NCC1CCNCC1] | N-[(piperidin-4-yl)methyl-5-(5-fluoro-2-oxo-1,2-dihydroindole-3-methylene)-2,4-dimethyl-1H-pyrrole-3-formamide |
| 5 | 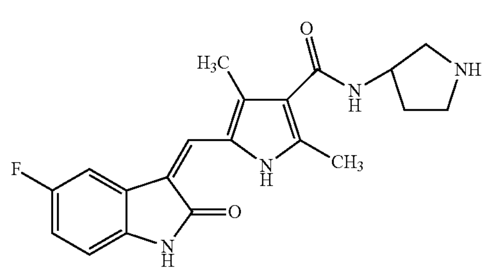 [SMILES: Cc1[nH]c(/C=C2\C(=O)Nc3ccc(F)cc32)c(C)c1C(=O)NC1CCNC1] | N-(pyrrolidin-3-yl)-5-(5-fluoro-2-oxo-1,2-dihydroindole-3-methylene)-2,4-dimethyl-1H-pyrrole-3-formamide |

-continued

| No. | Structure | Name |
|---|---|---|
| 6 | 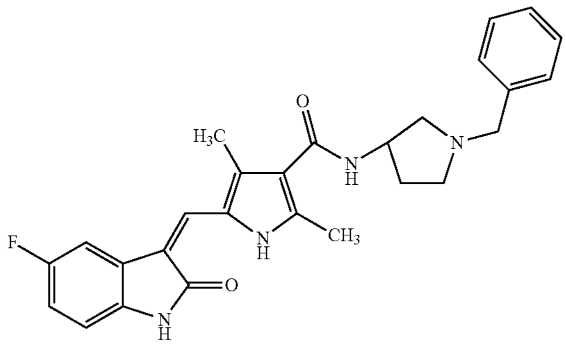 [SMILES: Cc1[nH]c(/C=C2\C(=O)Nc3ccc(F)cc32)c(C)c1C(=O)NC1CCN(Cc2ccccc2)C1] | N-(1-benzylpyrrolidin-3-yl)-5-(5-fluoro-2-oxo-1,2-dihydroindole-3-methylene)-2,4-dimethyl-1H-pyrrole-3-formamide |
| 7 | 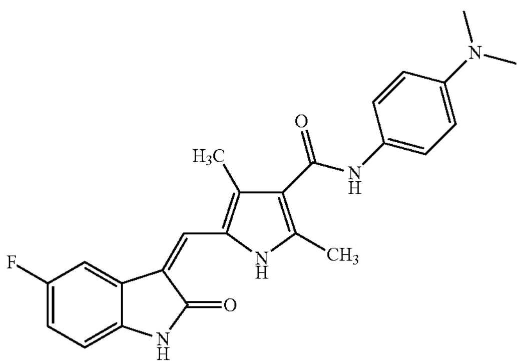 [SMILES: Cc1[nH]c(/C=C2\C(=O)Nc3ccc(F)cc32)c(C)c1C(=O)Nc1ccc(N(C)C)cc1] | N-[4-(dimethylamino)phenyl]-5-(5-fluoro-2-oxo-1,2-dihydroindole-3-methylene)-2,4-dimethyl-1H-pyrrole-3-formamide |
| 8 | 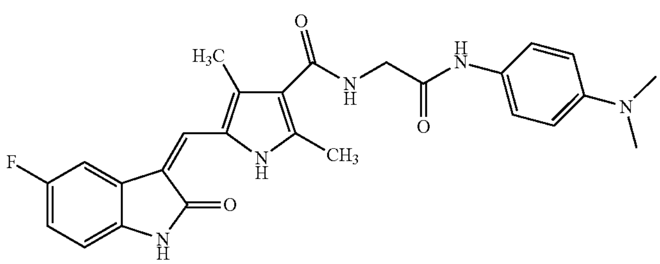 [SMILES: Cc1[nH]c(/C=C2\C(=O)Nc3ccc(F)cc32)c(C)c1C(=O)NCC(=O)Nc1ccc(N(C)C)cc1] | N-{2-[4-(dimethylamino)anilino]-2-oxoethyl}-5-(5-fluoro-2-oxo-1,2-dihydroindole-3-methylene)-2,4-dimethyl-1H-pyrrole-3-formamide |
| 9 | 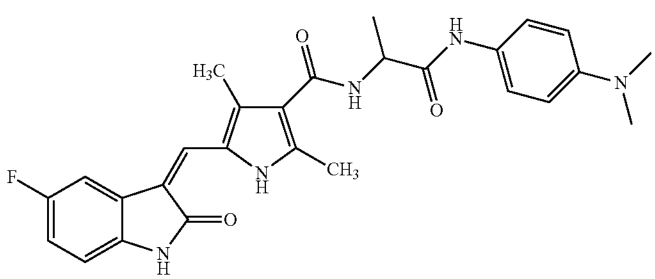 [SMILES: Cc1[nH]c(/C=C2\C(=O)Nc3ccc(F)cc32)c(C)c1C(=O)NC(C)C(=O)Nc1ccc(N(C)C)cc1] | N-{1-[4-(dimethylamino)anilino]-1-oxoprop-2-yl}-5-(5-fluoro-2-oxo-1,2-dihydroindole-3-methylene)-2,4-dimethyl-1H-pyrrole-3-formamide |
| 10 | 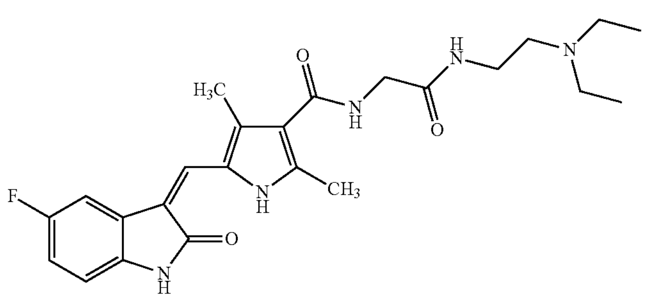 [SMILES: CCN(CC)CCNC(=O)CNC(=O)c1c(C)[nH]c(/C=C2\C(=O)Nc3ccc(F)cc32)c1C] | N-{2-[2-(diethylamino)ethylamino]-2-oxoethyl}-5-(5-fluoro-2-oxo-1,2-dihydroindole-3-methylene)-2,4-dimethyl-1H-pyrrole-3-formamide |

| No. | Structure | Name |
|---|---|---|
| 11 | 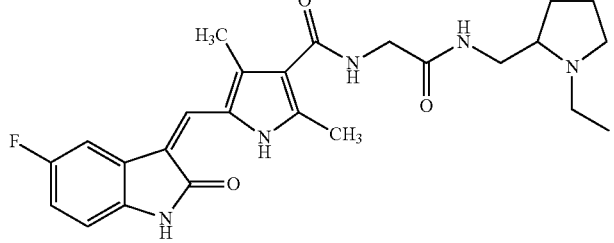 | N-{2-[(1-ethylpyrrolidin-2-yl)methylamino]-2-oxoethyl}-5-(5-fluoro-2-oxo-1,2-dihydroindole-3-methylene)-2,4-dimethyl-1H-pyrrole-3-formamide |
| 12 | 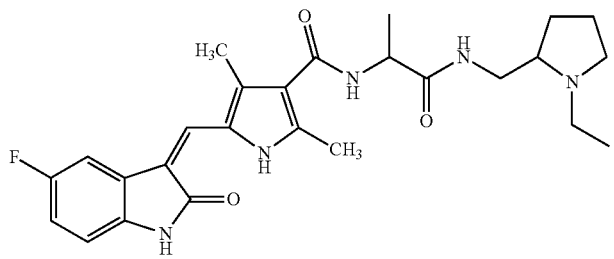 [SMILES: CCN1CCCC1CNC(=O)C(C)NC(=O)c1c(C)[nH]c(/C=C2\C(=O)Nc3ccc(F)cc32)c1C] | N-{2-[(1-ethylpyrrolidin-2-yl)methylamino]-1-oxoprop-2-yl}-5-(5-fluoro-2-oxo-1,2-dihydroindole-3-methylene)-2,4-dimethyl-1H-pyrrole-3-formamide |
| 13 | 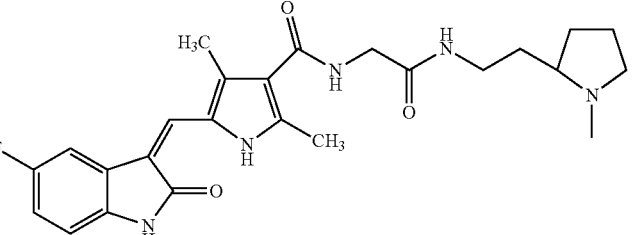 | N-{2-[2-(1-methylpyrrolidin-2-yl)ethylamino]-2-oxoethyl}-5-(5-fluoro-2-oxo-1,2-dihydroindole-3-methylene)-2,4-dimethyl-1H-pyrrole-3-formamide |
| 14 | 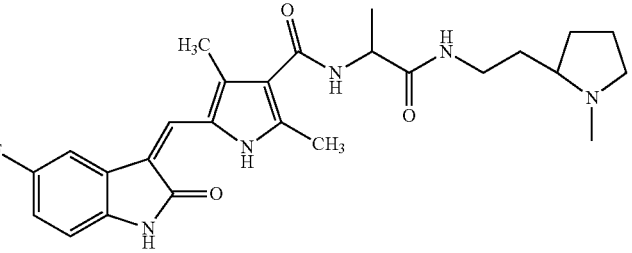 | N-{1-[2-(1-methylpyrrolidin-2-yl)ethylamino]-1-oxoprop-2-yl}-5-(5-fluoro-2-oxo-1,2-dihydroindole-3-methylene)-2,4-dimethyl-1H-pyrrole-3-formamide |
| 15 | 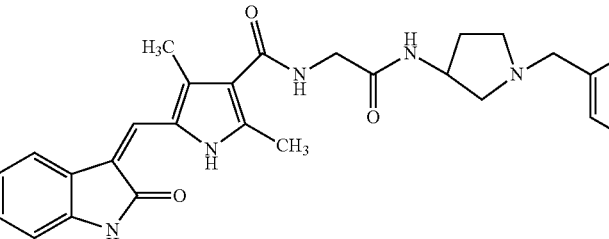 | N-{2-[(1-benzylpyrrolidin-3-yl)amino]-2-oxoethyl}-5-(5-fluoro-2-oxo-1,2-dihydroindole-3-methylene)-2,4-dimethyl-1H-pyrrole-3-formamide |
| 16 | 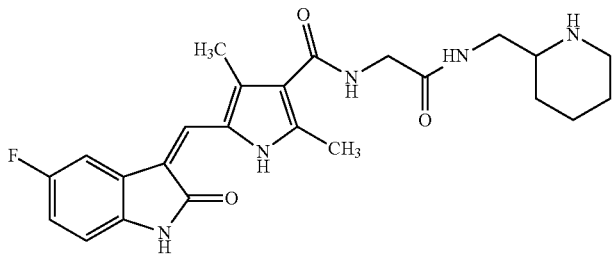 [SMILES: Cc1[nH]c(/C=C2\C(=O)Nc3ccc(F)cc32)c(C)c1C(=O)NCC(=O)NCC1CCCCN1] | N-{2-[(piperidin-2-yl)methylamino]-2-oxoethyl}-5-(5-fluoro-2-oxo-1,2-dihydroindole-3-methylene)-2,4-dimethyl-1H-pyrrole-3-formamide |

| No. | Structure | Name |
|---|---|---|
| 17 | (structure) | N-{2-[(piperidin-4-yl)methylamino]-2-oxoethyl}-5-(5-fluoro-2-oxo-1,2-dihydroindole-3-methylene)-2,4-dimethyl-1H-pyrrole-3-formamide |

The compounds of formula I may comprise asymmetric substituents, such as the asymmetric substituents in $R^8$ and/or $R^9$, which can result in formation of different stereoisomers, such as enantiomers, cis-trans isomers, etc. All the stereoisomers (enantiomers, diastereomers and cis-trans isomers) of compounds of formula I and mixtures thereof fall into the scope of the invention.

The invention disclosed herein is also intended to cover in vivo metabolites of the compounds of formula I. Such metabolites could be generated by such as oxidation, reduction, hydrolysis, amidation, esterification and the like of the administered compounds. Metabolites that can regulate protein kinase activity are principally produced through enzyme process.

The term "pharmaceutically acceptable salts thereof" refers to salts, while administered to a subject, being able to (directly or indirectly) provide compounds described herein. They maintain bioavailability and property of a free base (acid), and will not be undesirable in biological or other aspects. However, it is should be understood that non-pharmaceutically acceptable salts of the compounds of formula I fall within the scope of the invention as well, as they can be used for preparing pharmaceutically acceptable salts.

The compounds of formula I provided herein may work alone or in the form of pharmaceutically acceptable salts thereof. The "pharmaceutically acceptable salts" comprise acid addition salts of the compounds of formula I. Generally, such salts are prepared for example by reacting these compounds in free base form with stoichiometric amount of appropriate acids in water or organic solvents or mixtures thereof. Examples of pharmaceutically acceptable acid addition salts include inorganic acid addition salts, such as hydrochloride, hydrobromide, hydriodate, phosphate, metaphosphate, nitrate and sulfate. and organic acid addition salts, such as tartrate, acetate, trifluoroacetate, citrate, oxalate, malate, lactate, fumarate, benzoate, maleate, fumarate, mandelate, glycollate, gluconate, succinate, methanesulfonate and aryl sulfonate, such as p-toluenesulfonate. Salts of compounds of formula I further include the salts formed by replacing acid protons in the compounds of formula I with metal ions such as alkali metal ions, alkaline earth metal ions or aluminium ion, or complexes formed with organic bases (eg. ethanolamine, diethanolamine, triethanolamine, trihydroxymethylaminomethane, N-methylglucosamine, etc.). The salts of compounds of formula I are preferably organic acid addition salts, more preferably L-malic acid addition salts.

Another aspect of the invention relates to a method for preparing the compounds of formula I as defined above, comprising reacting a corresponding dihydroindolone intermediate of formula III with an appropriate intermediate of formula IV in the presence of an alkali:

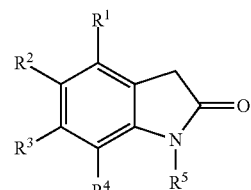

Formula III

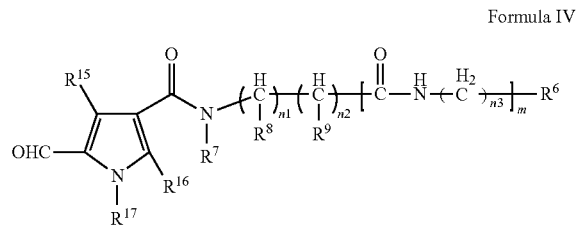

Formula IV wherein $R^1 \sim R^9$, $R^{15} \sim R^{17}$, n1, n2, n3 and m have the same meanings as defined in formula I.

The specific reaction conditions of the method for preparing the compounds of formula I are: heating the intermediate of formula IV (1 eq.) and the dihydroindolone intermediate of formula III (1 eq.) in alcoholic solvents under reflux for 3-6 h in the presence of the alkali, and then cooling to room temperature, filtering and collecting the solid. After purifying by recrystallization and drying, the compounds of formula I are obtained.

Another aspect of the invention relates to a method for preparing the compounds of formula II, comprising reacting a 5-fluoro-2-indolone intermediate of formula V with an intermediate of formula VI:

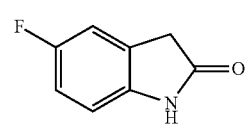

Formula V

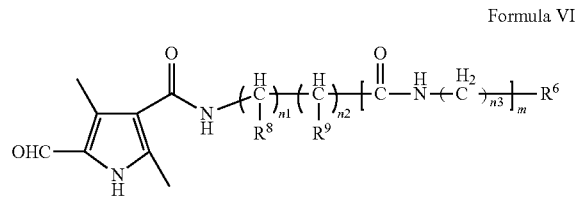

Formula VI wherein $R^6$, $R^8$, $R^9$, n1, n2, n3 and m have the same meanings as defined in formula II.

The specific reaction conditions of the method for preparing the compounds of formula II are similar with that of the method for preparing the compounds of formula I.

The alcoholic solvents used in the above methods include, but are not limited to, methanol, ethanol, n-propanol, isopropanol, n-butanol, isobutanol, t-butanol, n-pentanol, n-hexanol, or a mixture of two or more of them and the like. The choice of suitable organic alcohols can be made by those skilled in the art on the basis of known general principles of organic synthesis and the disclosure of the invention.

The alkalis used in the method are generally organic alkali, and include, but not limited to, pyrrolidine, triethylamine and the like. The choice of suitable organic alkalis can be determined by those skilled in the art on the basis of known general principles of organic synthesis and the disclosure of the invention.

Another aspect of the invention relates to an intermediate for preparing the compound of formula II: a compound of formula VI Formula VI

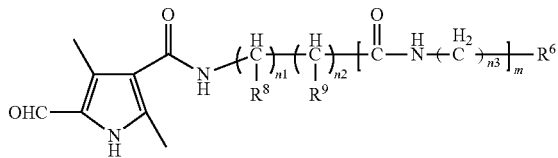

wherein $R^6$, $R^8$, $R^9$, n1, n2, n3 and m have the same meanings as defined in formula II.

Another aspect of the invention provides a method for preparing the intermediate compound of formula VI, comprising reacting a compound of formula VII with a compound of formula VIII below, which may be carried out according to the process for synthesis of acylamide known in the art. For example, a compound of formula VII and a compound of formula VIII were added to DMF under stirring in the presence of 1-ethyl-(3-dimethylaminopropyl) carbodiimide hydrochloride and triethylamine at low temperatures, and the reaction was performed until the intermediate compound of formula VI is obtained.

Formula VII

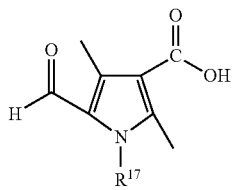

Formula VIII

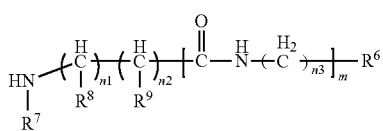

Another aspect of the invention relates to a pharmaceutical composition comprising a compound of formula I or a salt thereof or a compound of formula II or a salt thereof, preferably a pharmaceutically acceptable salt, and one or more pharmaceutically acceptable carriers, excipients and/or vehicles, for administering to an organism.

"Pharmaceutical compositions" refer to formulations comprising one or more compounds of the invention or salts thereof and carriers, excipients and/or vehicles generally accepted in the art for delivering bioactive compounds to an organism, such as human. The object of the pharmaceutical compositions is to contribute to administration of the compounds of the invention to an organism.

The term "pharmaceutically acceptable carriers" refers to those carriers and diluents which have no significant stimulating effects on an organism and will not damage the biological activities and properties of the active compounds. "Pharmaceutically acceptable excipients and/or vehicles" refer to inert substances administered together with active compounds and advantageous for the administration of them. "Pharmaceutically acceptable carriers, excipients and/or vehicles" include, but are not limited to, any carriers, excipients, vehicles, flow aids, sweeteners, diluents, antiseptics, dyes/colorants, flavoring agents, surfactants, wetting agents, dispersants, disintegrating agents, suspending agents, stabilizers, isotonizing agents, solvents or emulsifiers, which are approved by FDA to be acceptable for human or domestic animals. Non-limiting exemplary excipients include calcium carbonate, calcium phosphate, various sugars and starches, cellulose derivatives, gelatin, vegetable oils and polyethylene glycols.

The administration of the compounds of the invention or pharmaceutically acceptable salts thereof, in pure form or in the form of suitable pharmaceutical compositions, can be carried out through any acceptable administration routes for providing agents for similar use. The pharmaceutical compositions of the invention may be prepared by combining the compounds of the invention with suitable pharmaceutically acceptable carriers, excipients and/or vehicles, and formulated into solid, semi-solid, liquid, or gas preparations, such as tablets, pills, capsules, powders, granules, ointments, emulsions, suspensions, solutions, suppositories, injections, inhalants, gels, microspheres and aerosols, etc.

Representative administration routes of the compounds of the invention or pharmaceutically acceptable salts thereof or pharmaceutical compositions thereof include, but not limited to, oral, rectal, transmucosal, transrectal delivery, or topical, transdermal, inhalational, parenteral, sublingual, endovaginal, intranasal, intraocular, intraperitoneal, intramuscular, subcutaneous, intravenous delivery. Oral delivery is preferred.

The pharmaceutical compositions of the invention may be prepared by well known processes in the art, such as conventional processes of mixing, dissolution, granulation, manufacturing sugar-coated pills, levigating, emulsifying, freeze-drying etc.

In preferred embodiments, the pharmaceutical compositions are for oral delivery. For oral delivery, the pharmaceutical compositions may be formulated by mixing the active compounds with pharmaceutically acceptable carriers, excipients and/or vehicles well-known in the art. These carriers, excipients and vehicles allow the compounds of the invention to be formulated into tablets, pills, pastilles, sugar-coated agents, capsules, liquids, gels, syrups, suspensions and the like, for oral administration to patients.

Solid oral compositions may be prepared by conventional mixing, packing or tabletting methods. For example, they can be obtained by mixing the active compounds with solid excipients, optionally grinding the resultant mixture, adding other suitable adjuvants if necessary, and then processing the mixture into granules to obtain tablets or cores of sugar-coated agents. Suitable excipients include, but not limited to, fillers, such as sugars, including lactose, sucrose, mannitol or sorbitol, cellulose preparations, such as corn starch, wheat starch, rice starch and potato starch, and other materials, such as gelatin, tragacanth gum, methylcellulose, hydroxypropyl methylcellulose, hydroxymethyl cellulose sodium and/or polyvinylpyrrolidone, disintegrating agents, such as crosslinked polyvinylpyrrolidone, agar or alginic acid, and salts may also be used, such as alginate sodium. The cores of sugar coated agents may be optionally coated according to processes generally well-known in pharmaceutical practice, particularly coated with enteric coating.

The pharmaceutical compositions may also be used for parenteral administration, such as suitable aseptic solutions, suspensions or freeze-dried products in unit dosage forms. Suitable excipients, such as fillers, buffering agents or surfactants can be used.

As mentioned above, aberrant protein tyrosine kinase activity due to mutation or over-expression is associated with various diseases. For example, aberrant activities of receptor type protein tyrosine kinases EGFR and VEGFR are associated with human malignant tumors. EGFR (HER-1) family is overexpressed in tumors at ovarium, head and neck, esophagus, cervix, bladder, mammary gland, colon rectum, stomach and endometrium etc. HER-2 is overexpressed in breast cancer, ovarian cancer, prostate cancer, lung cancer and osteocarcinoma etc. C-KIT tyrosine kinases are associated with gastrointestinal stromal tumor and small cell lung cancer. The expression of VEGFR in lung cancer strongly correlates with poor survival rate in lung cancer, and plays an important role in colorectal cancer.

As another example, aberrant protein tyrosine kinase activity is also associated with diseases other than tumors: psoriasis (Dvir et al, J. Cell. Biol. 1991, 113, 857-865), fibrosis, cardiovascular diseases, such as atherosclerosis, restenosis (Buchdunger et al, Proc. Natl. Acad. Sci. USA. 1991, 92, 2258-2262), immune diseases, such as autoimmune diseases, anaphylaxis, asthma, graft rejection (Klausner and Samelson, Cell. 1991, 64, 875-878), inflammation (Berkois, Blood. 1992, 79 (9), 2446-2454), vascular development, thrombus formation (Salari et al, FEBS. 1990, 263 (1), 104-108), nervous system diseases (Ohmichi et al, Biochemistry, 1992, 31, 4034-4039), hepatocirrhosis, diabetes, ophthalmopathies, atrophic arthritis, and various nephropathies.

Another aspect of the invention relates to a method for treating and/or preventing protein tyrosine kinases associated diseases, comprising administering to a subject in need thereof a therapeutically effective amount of the compounds of formula I or salts or pharmaceutical compositions thereof, or the compounds of formula II or salts or pharmaceutical compositions thereof. The protein tyrosine kinases associated diseases are tumors, psoriasis, fibrosis, cardiovascular diseases, such as atherosclerosis, restenosis, immune diseases, such as autoimmune diseases, anaphylaxis, asthma, graft rejection, inflammation, vascular development, thrombus formation, nervous system diseases, hepatocirrhosis diabetes, ophthalmopathies, atrophic arthritis, and various nephropathies. In these diseases, tumors are preferred protein tyrosine kinase associated diseases.

Another aspect of the invention relates to a method for treating and/or preventing tumors, comprising administering to a subject in need thereof therapeutically effective amount of the compounds of formula I or salts or pharmaceutical compositions thereof, or the compounds of formula II or salts or pharmaceutical compositions thereof. Examples of the tumors include, but not limited to, cervical carcinoma, liver cancer, lung cancer, gastric cancer, breast cancer, bladder cancer, head and neck cancer, ovarian cancer, prostate cancer, colorectal cancer, genitourinary tract cancer, melanoma, squamous cell carcinoma, astrocyte cancer, kaposi sarcoma, and spongioblast cancer. Representative examples are cervical carcinoma, liver cancer, lung cancer, gastric cancer, and breast cancer etc.

Another aspect of the invention further relates to a method for treating and/or preventing fibroblast proliferation associated diseases, comprising administering to a subject in need thereof a therapeutically effective amount of the compounds of formula I or salts or pharmaceutical compositions thereof, or the compounds of formula II or salts or pharmaceutical compositions thereof. The tissue and organ fibrosis is a common feature of such diseases, and the proliferation of numerous fibrous connective tissues is a common pathogenesis of such diseases.

Examples of the fibroblast proliferation associated diseases, i.e., diseases of tissue and organ fibrosis include, but not limited to, pulmonary fibrosis, hepatic fibrosis, chronic pancreatitis, scleroderma, renal glomerular fibrosis, renal interstitial fibrosis and multiple organ fibrosis supervened with radiochemotherapy and tissue transplantation, etc. The pulmonary fibrosis is "diffuse pulmonary interstitial disease". The hepatic fibrosis is the lesion mainly manifested by diffuse proliferation of fibrous connective tissue in the liver. The chronic pancreatitis is the lesion caused by various factors and mainly manifested by the destruction of pancreatic cells and progressive fibrosis. The scleroderma is a connective tissue disease characterized by tissue fibrosis, vasculitis obliterans and production of numerous autoantibodies.

EXAMPLES

The following examples are given to enable those skilled in the art to more clearly understand and to carry out the invention. They should not be considered as limiting the scope of the invention, but only illustration and representatives of the invention. Those skilled in the art should understand that: there remain other synthetic schemes to obtain the compounds of the invention, and the following are provided as non-limiting examples.

Example 1

Synthesis of N-[(1-ethylpyrrolidin-2-yl)methyl]-5-formyl-2,4-dimethyl-1H-pyrrole-3-formamide 1-Ethyl-(3-dimethylaminopropyl) carbodiimide hydrochloride (268.1 g, 1.4 mol), triethylamine (280.0 mL), 5-formyl-2,4-dimethyl-1H-pyrrole-3-formic acid (167.0 g, 1.0 mol) and 1-hydroxybenzotriazole (189.2 g, 1.4 mol) were added to DMF (500 mL) with stirring at about 0° C. and allowed to stir for 1.5 hrs, and then (1-ethylpyrrolidin-2-yl) methylamine (1.2 mol) was added. The reaction was stirred at room temperature until completion was indicated by thin layer chromatography (TLC). 120 mL of water and 100 mL of saturated salt water were added, and the mixture was extracted with 10% methanol/dichloromethane (300 mL×3). The combined organic phase was washed with saturated salt water (300 mL×3), dried over anhydrous $Na_2SO_4$, and the solvent was distilled off under reduced pressure. The residue was chromatographed on silica gel (eluted with methanol/ethyl acetate=1/1) to afford 131.86 g (476 mmol) of N-[(1-ethylpyrrolidin-2-yl) methyl]-5-formyl-2,4-dimethyl-1H-pyrrole-3-formamide as an off-white solid. Yield 47.6%, m.p. 166-169° C.

Example 2

Synthesis of N-[(1-ethylpyrrolidin-2-yl)methyl]-5-(5-fluoro-2-oxo-1,2-dihydroindole-3-methylene)-2,4-dimethyl-1H-pyrrole-3-formamide (Compound 1)

N-[(1-ethylpyrrolidin-2-yl)methyl]-5-formyl-2,4-dimethyl-1H-pyrrole-3-formamide (277 g, 1.0 mol), 5-fluoro-2-indolone (151 g, 1.0 mol), ethanol (2 L) and pyrrolidine (4 mL) were mixed and heated to 78° C. with stirring, and allowed to react at this temperature for 3 hrs, then cooled to room temperature, filtered and the collected solid was recrystallized from ethanol, dried to give 311.6 g (760 mmol) of N-[(1-ethylpyrrolidin-2-yl)methyl]-5-(5-fluoro-2-oxo-1,2-dihydroindole-3-methylene)-2,4-dimethyl-1H-pyrrole-3-formamide as a saffron solid. Yield 76.0%, m.p. 232-236° C. $^1$HNMR (DMSO-d6) δ13.65 (s, br, 1H, NH), 10.80 (s, br, 1H, NH), 7.72 (s, 1H, methylene hydrogen), 7.37 (t, br, 1H, NH), 6.81-6.92 (m, 3H, benzene ring hydrogen), 3.13-3.31 (q, 2H), 3.03-3.07 (q, 2H), 2.81-2.85 (m, 2H), 2.80-2.83 (m, 1H), 2.42 (s, 3H), 2.48 (s, 3H), 2.23-2.25 (q, 2H), 1.66-2.09 (m, 2H), 1.02-1.05 (t, 3H).

Example 3

Synthesis of N-[(1-methylpyrrolidin-2-yl)ethyl]-5-formyl-2,4-dimethyl-1H-pyrrole-3-formamide 1-Ethyl-(3-dimethylaminopropyl) carbodiimide hydrochloride (268.1 g, 1.4 mol), triethylamine (280.0 mL), 5-formyl-2,4-dimethyl-1H-pyrrole-3-formic acid (167.0 g, 1.0 mol) and 1-hydroxybenzotriazole (189.2 g, 1.4 mol) were sequentially added to DMF (500 mL) with stirring at about 0° C., and stirred for 1.5 hrs, then (1-methylpyrrolidin-2-yl)ethylamine (1.2 mol) was added. The reaction was stirred at room temperature until completion was indicated by thin layer chromatography (TLC). 120 mL of water and 100 mL of saturated salt water were added, and the mixture was extracted with 10% methanol/dichloromethane (300 mL×3), the combined organic phase was washed with saturated salt water (300 mL×3), dried over anhydrous Na$_2$SO$_4$, and the solvent was distilled off under reduced pressure. The residue was then chromatographed on silica gel (eluted with methanol/ethyl acetate=1/1) to give 139.1 g (502 mmol) of N-[(1-methylpyrrolidin-2-yl)ethyl]-5-formyl-2,4-dimethyl-1H-pyrrole-3-formamide as an off-white solid. Yield 50.2%, m.p. 143-149° C.

Example 4

Synthesis of N-[(1-methylpyrrolidin-2-yl)ethyl]-5-(5-fluoro-2-oxo-1,2-dihydroindole-3-methylene)-2,4-dimethyl-1H-pyrrole-3-formamide (Compound 2)

N-[(1-methylpyrrolidin-2-yl)ethyl]-5-formyl-2,4-dimethyl-1H-pyrrole-3-formamide (277.1 g, 1.0 mol), 5-fluoro-2-indolone (151 g, 1.0 mol), ethanol (2 L) and pyrrolidine (4 mL) were mixed and heated to 78° C. with stirring, and allowed to react at this temperature for 3 hrs, cooled to room temperature, filtered and the collected solid was recrystallized from ethanol, dried to give 346.5 g (845 mmol) of N-[(1-methylpyrrolidin-2-yl)ethyl]-5-(5-fluoro-2-oxo-1,2-dihydroindole-3-methylene)-2,4-dimethyl-1H-pyrrole-3-formamide as a saffron solid. Yield 84.5%, m.p. 241-244° C. $^1$HNMR (DMSO-d6) δ 13.65 (s, br, 1H, NH), 10.81 (s, br, 1H, NH), 7.73 (s, 1H, methylene hydrogen), 7.62 (t, br, 1H, NH), 6.84-6.94 (m, 3H, benzene ring hydrogen), 3.39-3.43 (m, 1H), 3.21-3.25 (t, 2H), 2.51 (s, 3H), 2.52 (s, 3H), 2.22 (s, 3H), 2.08-2.11 (m, 2H), 1.82-1.86 (m, 2H), 1.58-1.64 (m, 2H), 1.39-1.44 (m, 2H).

Example 5

Synthesis of N-[(piperidin-2-yl)methyl]-5-formyl-2,4-dimethyl-1H-pyrrole-3-formamide 1-Ethyl-(3-dimethylaminopropyl) carbodiimide hydrochloride (268.1 g, 1.4 mol), triethylamine (280.0 mL), 5-formyl-2,4-dimethyl-1H-pyrrole-3-formic acid (167.0 g, 1.0 mol) and 1-hydroxybenzotriazole (189.2 g, 1.4 mol) were sequentially added to DMF (500 mL) with stirring at about 0° C. and stirred for 1.5 hrs, then piperidin-2-yl-methylamine (1.2 mol) was added. The reaction was stirred at room temperature until completion was indicated by thin layer chromatography (TLC). 120 mL of water and 100 mL of saturated salt water were added, and the mixture was extracted with 10% methanol/dichloromethane (300 mL×3), the combined organic phase was washed with saturated salt water (300 mL×3), dried over anhydrous Na$_2$SO$_4$, and the solvent was distilled off under reduced pressure. The residue was then chromatographed on silica gel (eluted with methanol/ethyl acetate=1/1) to give 117.8 g (448 mmol) of N-[(piperidin-2-yl)methyl]-5-formyl-2,4-dimethyl-1H-pyrrole-3-formamide as an off-white solid. Yield 44.8%, m.p. 107-115° C.

Example 6

Synthesis of N-[(piperidin-2-yl)methyl-5-(5-fluoro-2-oxo-1,2-dihydroindole-3-methylene)-2,4-dimethyl-1H-pyrrole-3-formamide (compound 3)

N-[(piperidin-2-yl)methyl]-5-formyl-2,4-dimethyl-1H-pyrrole-3-formamide (262.9 g, 1.0 mol), 5-fluoro-2-indolone (151 g, 1.0 mol), ethanol (2 L) and pyrrolidine (4 mL) were mixed and heated to 78° C. with stirring, and allowed to react at this temperature for 3 hrs, cooled to room temperature, filtered and the collected solid was recrystallized from ethanol, dried to give 307.3 g (776 mmol) of N-[(piperidin-2-yl)methyl-5-(5-fluoro-2-oxo-1,2-dihydroindole-3-methylene)-2,4-dimethyl-1H-pyrrole-3-formamide as a saffron solid. Yield 77.6%, m.p. 263-266° C. $^1$HNMR (DMSO-d6) δ13.67 (s, br, 1H, NH), 10.82 (s, br, 1H, NH), 7.74 (s, 1H, methylene), 7.49 (t, br, 1H, NH), 6.83-6.94 (m, 3H, benzene ring hydrogen), 4.40 (s, br, 1H, NH), 3.39-3.43 (m, 1H), 3.16-3.18 (m, 2H), 2.50 (s, 3H), 2.60 (s, 3H), 2.08-2.11 (m, 2H), 1.82-1.86 (m, 2H), 1.58-1.64 (m, 2H), 1.39-1.44 (m, 2H).

Example 7

Synthesis of N-[(piperidin-4-yl)methyl]-5-formyl-2,4-dimethyl-1H-pyrrole-3-formamide 1-Ethyl-(3-dimethylaminopropyl) carbodiimide hydrochloride (268.1 g, 1.4 mol), triethylamine (280.0 mL), 5-formyl-2,4-dimethyl-1H-pyrrole-3-formic acid (167.0 g, 1.0 mol) and 1-hydroxybenzotriazole (189.2 g, 1.4 mol) were added to DMF (500 mL) with stirring at about 0° C. and stirred for 1.5 hrs, then piperidin-4-yl-methylamine (1.2 mol) was added. The reaction was stirred at room temperature until completion was indicated by thin layer chromatography (TLC). 120 mL of water and 100 mL of saturated salt water were added, and the mixture was extracted with 10% methanol/dichloromethane (300 mL×3), the combined organic phase was washed with saturated salt water (300 mL×3), dried over anhydrous $Na_2SO_4$, and the solvent was distilled off under reduced pressure. The residue was then chromatographed on silica gel (eluted with methanol/ethyl acetate=1/1) to give 158.3 g (602 mmol) of N-[(piperidin-4-yl)methyl]-5-formyl-2,4-dimethyl-1H-pyrrole-3-formamide as an off-white solid. Yield 60.2%.

Example 8

Synthesis of N-[(piperidin-4-yl)methyl-5-(5-fluoro-2-oxo-1,2-dihydro indole-3-methylene)-2,4-dimethyl-1H-pyrrole-3-formamide (Compound 4)

N-[(piperidin-4-yl)methyl]-5-formyl-2,4-dimethyl-1H-pyrrole-3-formamide (263.0 g, 1.0 mol), 5-fluoro-2-indolone (151 g, 1.0 mol), ethanol (2 L) and pyrrolidine (4 mL) were mixed and heated to 78° C. with stirring, and allowed to react at this temperature for 3 hrs, then cooled to room temperature, filtered and the collected solid was recrystallized from ethanol, dried to give 258.2 g (652 mmol) of N-[(piperidin-4-yl)methyl-5-(5-fluoro-2-oxo-1,2-dihydroindole-3-methylene)-2,4-dimethyl-1H-pyrrole-3-formamide as a saffron solid. Yield 65.2%. $^1$HNMR (DMSO-d6) δ13.66 (s, br, 1H, NH), 10.82 (s, br, 1H, NH), 7.68-7.74 (m, 3H, benzene ring hydrogen), 7.62 (t, br, 1H, NH), 6.83 (s, 1H, methylene hydrogen), 4.41 (s, br, 1H, NH), 3.67-3.68 (m, 1H), 3.50-3.66 (m, 2H), 3.16-3.17 (m, 2H), 2.50 (s, 3H), 2.60 (s, 3H), 1.71-1.82 (m, 2H), 1.10-1.11 (m, 2H).

Example 9

Synthesis of N-(pyrrolidin-3-yl)-5-formyl-2,4-dimethyl-1H-pyrrole-3-formamide

1-Ethyl-(3-dimethylaminopropyl) carbodiimide hydrochloride (268.1 g, 1.4 mol), triethylamine (280.0 mL), 5-formyl-2,4-dimethyl-1H-pyrrole-3-formic acid (167.0 g, 1.0 mol) and 1-hydroxybenzotriazole (189.2 g, 1.4 mol) were added to DMF (500 mL) with stirring at about 0° C. and stirred for 1.5 hrs, then pyrrolidine-3-amine (1.2 mol) was added. The reaction was stirred at room temperature until completion was indicated by thin layer chromatography (TLC). 120 mL of water and 100 mL of saturated salt water were added, and the mixture was extracted with 10% methanol/dichloromethane (300 mL×3), the combined organic phase was washed with saturated salt water (300 mL×3), dried over anhydrous $Na_2SO_4$, and the solvent was distilled off under reduced pressure. The residue was then chromatographed on silica gel (eluted with methanol/ethyl acetate=1/1) to give 159.8 g (680 mmol) of N-(pyrrolidin-3-yl)-5-formyl-2,4-dimethyl-1H-pyrrole-3-formamide as an off-white solid. Yield 68.0%.

Example 10

Synthesis of N-(pyrrolidin-3-yl)-5-(5-fluoro-2-oxo-1,2-dihydroindole-3-methylene)-2,4-dimethyl-1H-pyrrole-3-formamide (Compound 5)

N-(pyrrolidin-3-yl)-5-formyl-2,4-dimethyl-1H-pyrrole-3-formamide (235 g, 1.0 mol), 5-fluoro-2-indolone (151 g, 1.0 mol), ethanol (2 L) and pyrrolidine (4 mL) were mixed and heated to 78° C. with stirring, and allowed to react at this temperature for 3 hrs, then cooled to room temperature, filtered and the collected solid was recrystallized from ethanol, dried to give 326.0 g (886 mmol) of N-(pyrrolidin-3-yl)-5-(5-fluoro-2-oxo-1,2-dihydroindole-3-methylene)-2,4-dimethyl-1H-pyrrole-3-formamide as a saffron solid. Yield 88.6%. $^1$HNMR (DMSO-d6) δ 13.69 (s, br, 1H, NH), 10.69 (s, br, 1H, NH), 6.79-6.92 (m, 3H, benzene ring hydrogen), 7.26 (s, 1H, methylene), 6.92 (t, br, 1H, NH), 3.67-3.68 (m, 1H), 3.54-3.66 (m, 2H), 3.16-3.22 (m, 2H), 2.51 (s, 1H, NH), 2.32 (s, 3H), 2.33 (s, 3H), 1.71-1.82 (m, 2H).

Example 11

Synthesis of N-(1-benzylpyrrolidin-3-yl)-5-formyl-2,4-dimethyl-1H-pyrrole-3-formamide 1-Ethyl-(3-dimethylaminopropyl) carbodiimide hydrochloride (268.1 g, 1.4 mol), triethylamine (280.0 mL), 5-formyl-2,4-dimethyl-1H-pyrrole-3-formic acid (167.0 g, 1.0 mol) and 1-hydroxybenzotriazole (189.2 g, 1.4 mol) were added to DMF (500 mL) with stirring at about 0° C. and stirred for 1.5 hrs, then 1-benzylpyrrolidine-3-amine (1.2 mol) was added. The reaction was stirred at room temperature until completion was indicated by thin layer chromatography (TLC). 120 mL of water and 100 mL of saturated salt water were added, and the mixture was extracted with 10% methanol/dichloromethane (300 mL×3), the combined organic phase was washed with saturated salt water (300 mL×3), dried over anhydrous $Na_2SO_4$, and the solvent was distilled off under reduced pressure. The residue was then chromatographed on silica gel (eluted with methanol/ethyl acetate=1/1) to give 170.3 g (524 mmol) of N-(1-benzylpyrrolidin-3-yl)-5-formyl-2,4-dimethyl-1H-pyrrole-3-formamide as an off-white solid. Yield 52.4%.

Example 12

Synthesis of N-(1-benzylpyrrolidin-3-yl)-5-(5-fluoro-2-oxo-1,2-dihydroindole-3-methylene)-2,4-dimethyl-1H-pyrrole-3-formamide (Compound 6)

N-(1-benzylpyrrolidin-3-yl)-5-formyl-2,4-dimethyl-1H-pyrrole-3-formamide (325 g, 1.0 mol), 5-fluoro-2-indolone (151 g, 1.0 mol), ethanol (2 L) and pyrrolidine (4 mL) were mixed and heated to 78° C. with stirring, and allowed to react at this temperature for 3 hrs, cooled to room temperature, filtered and the collected solid was recrystallized from ethanol, dried to give 360.4 g (787 mmol) of N-(1-benzylpyrrolidin-3-yl)-5-(5-fluoro-2-oxo-1,2-dihydroindole-3-methylene)-2,4-dimethyl-1H-pyrrole-3-formamide as a saffron solid. Yield 78.7%. $^1$HNMR (DMSO-d6) δ13.64 (s, br, 1H, NH), 10.81 (s, br, 1H, NH), 7.68-7.74 (m, 3H, benzene ring hydrogen), 7.26 (s, 1H, isopropyl), 6.92 (t, br, 1H, NH), 6.83-6.86 (m, 5H, benzene ring hydrogen), 3.67-3.68 (m, 1H), 3.50-3.669 (m, 2H), 3.16-3.17 (m, 2H), 2.32 (s, 3H), 2.33 (s, 3H), 1.71-1.82 (m, 2H), 1.10-1.11 (m, 2H).

Example 13

Synthesis of N-[4-(dimethylamino) phenyl]-5-formyl-2,4-dimethyl-1H-pyrrole-3-formamide 1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, then N,N-dimethyl-p-phenylenediamine (1.09 g, 8 mmol) was added. The reaction was stirred at room temperature until completion was indicated by thin layer chromatography (TLC). 1.2 mL of water and 1 mL of saturated salt water were added, and the mixture was extracted with 10% methanol/dichloromethane (25 mL×3), the combined organic phase was washed with saturated salt water (30 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.682 g (2.4 mmol) of N-[4-(dimethylamino) phenyl]-5-formyl-2,4-dimethyl-1H-pyrrole-3-formamide. Yield 59.9%. $^1$HNMR (DMSO-d6) δ 10.92 (s, br, 1H, NH), 9.64 (s, 9.34 (s, br, 1H, NH), 7.54-7.52 (d, 2H), 6.77-6.74 (d, 2H), 3.38-2.58 (s, 6H), 2.58-2.56 (m, 3H), 2.55-2.41), (m, 3H).

Example 14

Synthesis of N-{2-[4-(dimethylamino)anilino]-2-oxoethyl}-5-formyl-2,4-dimethyl-1H-pyrrole-3-formamide Chloroacetic chloride (4.52 g, 40 mmol) was added dropwise to a solution of N,N-dimethyl-p-phenylenediamine (5.48 g, 40 mmol) in dichloromethane (50 mL) with stirring at about 0° C. Afterwards, the reaction was warmed to room temperature and stirred until completion was indicated by thin layer chromatography (TLC). The dichloromethane was distilled off to give 8.1 g (38.2 mmol) of an oily residue. Yield 95.6%.

The oily residue obtained in the above step and aqueous ammonia (28%, 300 mL) were added to methanol solution (300 mL) and stirred at about 45° C. until completion was indicated by thin layer chromatography (TLC). The methanol was distilled off to give 5.9 g (30.8 mmol) of oily residue. Yield 80.6%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, then the oily residue obtained in the above step (1.54 g, 8 mmol) was added. The reaction was stirred at room temperature until completion was indicated by thin layer chromatography (TLC). 1.2 mL of water and 1 mL of saturated salt water were added, and the mixture was extracted with organic solvents (10% methanol/dichloromethane) (25 mL×3), the combined organic phase was washed with saturated salt water (25 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.85 g (2.49 mmol) of N-{2-[4-(dimethylamino) anilino]-2-oxoethyl}-5-formyl-2,4-dimethyl-1H-pyrrole-3-formamide. Yield 62.2%. $^1$HNMR (DMSO-d6) δ 10.83 (s, br, 1H, NH), 9.67 (s, 1H), 9.34 (s, br, 1H, NH), 7.65 (m, br, 1H, CONHCH$_2$), 7.54-7.52 (d, 2H), 6.77-6.74 (d, 2H), 3.81-3.73 (d, 2H), 3.38-2.58 (s, 6H), 2.58-2.56 (m, 3H), 2.55-2.41 (m, 3H).

Example 15

Synthesis of N-{1-[4-(dimethylamino)anilino]-1-oxoprop-2-yl}-5-formyl-2,4-dimethyl-1H-pyrrole-3-formamide 2-Bromopropionyl bromide (9.2 g, 40 mmol) was added dropwise to a solution of N,N-dimethyl-p-phenylenediamine (5.48 g, 40 mmol) in dichloromethane (50 mL) with stirring at about 0° C. Afterwards, the reaction was warmed to room temperature and stirred until completion was indicated by thin layer chromatography (TLC). The dichloromethane was distilled off to give 7.74 g (34.24 mmol) of an oily residue. Yield 85.6%.

The oily residue obtained in the above step and aqueous ammonia (28%, 300 mL) were added to methanol solution (300 mL) and stirred at about 45° C. until completion was indicated by thin layer chromatography (TLC). The methanol was distilled off to give 6.28 g (30.33 mmol) of an oily residue. Yield 88.6%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, and the oily residue obtained in the above step (1.66 g, 8 mmol) was added. The reaction was stirred at room temperature until completion was indicated by thin layer chromatography (TLC). 1.2 mL of water and 1 mL of saturated salt water were added, and the mixture was extracted with organic solvents (10% methanol/dichloromethane) (25 mL×3), the combined organic phase was washed with saturated salt water (25 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.786 g (2.21 mmol) of N-{1-[4-(dimethylamino) anilino]-1-oxoprop-2-yl}-5-formyl-2,4-dimethyl-1H-pyrrole-3-formamide, yield 55.2%. $^1$HNMR (DMSO-d6) δ 10.83 (s, br, 1H, NH), 9.67 (s, 1H), 9.34 (s, br, 1H, NH), 7.65 (m, br, 1H, CONHCH$_2$), 7.54-7.52 (d, 2H), 6.77-6.74 (d, 2H), 4.71 (m, 1H), 3.38-2.58 (s, 6H), 2.58-2.56 (m, 3H), 2.55-2.41 (m, 3H), 1.48-1.41 (d, 3H).

Example 16

Synthesis of N-{2-[2-(diethylamino) ethylamino]-2-oxoethyl}-5-formyl-2,4-dimethyl-1H-pyrrole-3-formamide Chloroacetic chloride (4.52 g, 40 mmol) was added dropwise to a solution of N,N-dimethyl-p-phenylenediamine (4.64 g, 40 mmol) in dichloromethane (50 mL) with stirring at about 0° C. Afterwards, the reaction was warmed to room temperature and stirred until completion was indicated by thin layer chromatography (TLC). The dichloromethane was distilled off to give 7.40 g (38.52 mmol) of an oily residue. Yield 96.3%.

The oily residue obtained in the above step and aqueous ammonia (28%, 300 mL) were added to methanol solution (300 mL) and stirred at about 45° C. until completion was indicated by thin layer chromatography (TLC). The methanol was distilled off to give 5.68 g (32.82 mmol) of oily residue. Yield 85.2%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, and the oily residue obtained in the above step (1.38 g, 8 mmol) was added. The reaction was stirred at room temperature until completion was indicated by thin layer chromatography (TLC). 1.2 mL of water and 1 mL of saturated salt water were added, and the mixture was extracted with organic solvents (10% methanol/dichloromethane) (25 mL×3), the combined organic phase was washed with saturated salt water (25 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.625 g (1.94 mmol) of N-{2-[2-(diethylamino)ethylamino]-2-oxoethyl}-5-formyl-2,4-dimethyl-1H-pyrrole-3-formamide. Yield 48.5%. $^1$HNMR (DMSO-d6) δ 10.83 (s, br, 1H, NH), 9.75 (s, 1H), 7.65 (m, br, 1H, CONHCH$_2$), 7.64 (m, br, 1H, CONHCH$_2$), 3.81-3.73 (d, 2H), 3.14-3.10 (m, 2H), 2.57-2.55 (m, 2H), 2.46-2.40 (m, 4H), 2.26-2.20 (s, 3H), 2.12-2.08 (m, 3H), 1.06-1.01 (m, 6H).

Example 17

Synthesis of N-{2-[(1-ethylpyrrolidin-2-yl)methylamino]-2-oxoethyl}-5-formyl-2,4-dimethyl-1H-pyrrole-3-formamide Chloroacetic chloride (4.52 g, 40 mmol) was added dropwise to a solution of (1-ethylpyrrolidin-2-yl)methylamine (5.68 g, 40 mmol) in dichloromethane (50 mL) with stirring at about 0° C. Afterwards, the reaction was warmed to room temperature and stirred until completion was indicated by thin layer chromatography (TLC). The dichloromethane was distilled off to give 7.39 g (36.12 mmol) of oily residue. Yield 90.3%.

The oily residue obtained in the above step and aqueous ammonia (28%, 300 mL) were added to methanol solution (300 mL) and stirred at about 45° C. until completion was indicated by thin layer chromatography (TLC). The methanol was distilled off to give 5.49 g (29.69 mmol) of an oily residue Yield 82.2%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were sequentially added to DMF (10 mL) with stirring at about 0° C. and stirred for 1.5 hrs, and the oily residue obtained in the above step (1.48 g, 8 mmol) was added. The reaction was stirred at room temperature until completion was indicated by thin layer chromatography (TLC). 1.2 mL of water and 1 mL of saturated salt water were added, and the mixture was extracted with organic solvents (10% methanol/dichloromethane) (25 mL×3), the combined organic phase was washed with saturated salt water (25 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.786 g (2.35 mmol) of N-{2-[(1-ethylpyrrolidin-2-yl)methylamino]-2-oxoethyl}-5-formyl-2,4-dimethyl-1H-pyrrole-3-formamide. Yield 58.8%. $^1$HNMR (DMSO-d6) δ10.83 (s, br, H, NH), 9.75 (s, 1H), 7.74 (m, br, 1H, CONHCH$_2$), 7.51 (m, br, 1H, CONHCH$_2$), 3.85-3.83 (d, 2H), 3.07-3.03 (m, 2H), 2.85 (m, 1H), 2.49-2.46 (m, 2H), 2.32-2.30 (m, 2H), 2.37-2.33 (m, 3H), 2.14-2.10 (m, 3H), 1.68-1.64 (m, 2H), 1.56-1.54 (m, 2H), 1.06-1.01 (m, 3H).

Example 18

Synthesis of N-{1-[(1-ethylpyrrolidin-2-yl)methylamino]-1-oxoprop-2-yl}-5-formyl-2,4-dimethyl-1H-pyrrole-3-formamide 2-Bromopropionyl bromide (9.2 g, 40 mmol) was added dropwise to a solution of (1-ethylpyrrolidin-2-yl)methylamine (5.68 g, 40 mmol) in dichloromethane (50 mL) with stirring at about 0° C. Afterwards, the reaction was warmed to room temperature and stirred until completion was indicated by thin layer chromatography (TLC). The solvent was distilled off to give 7.10 g (32.48 mmol) of an oily residue. Yield 81.2%.

The oily residue obtained in the above step and aqueous ammonia (300 mL) were added to methanol solution (300 mL) and stirred at about 45° C. until completion was indicated by thin layer chromatography (TLC). The solvent was distilled off to give 5.95 g (29.91 mmol) of an oily residue. Yield 92.1%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, and the oily residue obtained in the above step (1.59 g, 8 mmol) was added. The reaction was stirred at room temperature until completion was indicated by thin layer chromatography (TLC). 1.2 mL of water and 1 mL of saturated salt water were added, and the mixture was extracted with organic solvents (10% methanol/dichloromethane) (25 mL×3), the combined organic phase was washed with saturated salt water (25 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.696 g (2.0 mmol) of N-{1-[(1-ethylpyrrolidin-2-yl)methylamino]-1-oxoprop-2-yl}-5-formyl-2,4-dimethyl-1H-pyrrole-3-formamide. Yield 49.8%. $^1$HNMR (DMSO-d6) δ 10.83 (s, br, 1H, NH), 9.75 (s, 1H), 7.72 (m, br, 1H, CONHCH$_2$), 7.70 (m, br, 1H, CONHCH$_2$), 4.71 (m. 1H), 3.07-3.03 (m, 2H), 2.85 (m, 1H), 2.49-2.46 (m, 2H), 2.37-2.31 (m, 3H), 2.30 (m, 2H), 2.14-2.09 (m, 3H), 1.68-1.64 (m, 2H), 1.56-1.54 (m, 2H), 1.48-1.41 (d, 3H), 1.07-1.04 (m, 3H).

Example 19

Synthesis of N-{2-[2-(1-methylpyrrolidin-2-yl)ethylamino]-2-oxoethyl}-5-formyl-2,4-dimethyl-1H-pyrrole-3-formamide Chloroacetic chloride (4.52 g, 40 mmol) was added dropwise to a solution of 2-(1-methylpyrrolidin-2-yl)methylamine (5.68 g, 40 mmol) in dichloromethane (50 mL) with stirring at about 0° C. Afterwards, the reaction was warmed to room temperature and stirred until completion was indicated by thin layer chromatography (TLC). The solvent was distilled off to give 7.33 g (35.84 mmol) of an oily residue. Yield 89.6%.

The oily residue obtained in the above step and aqueous ammonia (300 mL) were added to methanol solution (300 mL) and stirred at about 45° C. until completion was indicated by thin layer chromatography (TLC). The solvent was distilled off to give 5.70 g (30.82 mmol) of an oily residue. Yield 86.0%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, and the oily residue obtained in the above step (1.48 g, 8 mmol) was added. The reaction was stirred at room temperature until completion was indicated by thin layer chromatography (TLC). 1.2 mL of water and 1 mL of saturated salt water were added, and the mixture was extracted with organic solvent (10% methanol/dichloromethane) (25 mL×3), the combined organic phase was washed with saturated salt water (25 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.783 g (2.34 mmol) of N-{2-[2-(1-methylpyrrolidin-2-yl)ethylamino]-5-formyl-2,4-dimethyl-2-oxoethyl}-1H-pyrrole-3-formamide. Yield 58.6%. $^1$HNMR (DMSO-d6) δ 10.83 (s, br, 1H, NH), 9.75 (s, 1H), 7.65 (m, br, 1H, CONHCH$_2$), 7.64 (m, br, 1H, CONHCH$_2$), 3.81-3.73 (d, 2H), 3.12-3.10 (m, 2H), 2.86 (m, 1H), 2.37-2.31 (m, 3H), 2.30-2.22 (m, 2H), 2.26-2.20 (s, 3H), 2.12-2.08 (m, 3H), 1.68-1.64 (m, 2H), 1.61-1.53 (m, 2H), 1.56-1.54 (m, 2H).

Example 20

Synthesis of N-{1-[2-(1-methylpyrrolidin-2-yl)ethylamino]-1-oxoprop-2-yl}-5-formyl-2,4-dimethyl-1H-pyrrole-3-formamide 2-Bromopropionyl bromide (9.2 g, 40 mmol) was added dropwise to a solution of 2-(1-methylpyrrolidin-2-yl)ethylamine (5.68 g, 40 mmol) in dichloromethane (50 mL) with stirring at about 0° C. Afterwards, the reaction was warmed to room temperature and stirred until thin layer chromatography (TLC) indicated complete reaction. The solvent was distilled off to afford an oily residue 7.96 g (36.52 mmol). Yield 91.3%.

The oily residue obtained in the above step and aqueous ammonia (300 mL) were added to methanol solution (300 mL) and allowed to stir at about 45° C. until completion was indicated by thin layer chromatography (TLC). The solvent was distilled off to give 6.49 g (32.6 μmol) of an oily residue. Yield 89.3%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, and the compound obtained in the above step (1.59 g, 8 mmol) was added. The reaction was stirred at room temperature until completion was indicated by thin layer chromatography (TLC). 1.2 mL of water and 1 mL of saturated salt water were added, and the mixture was extracted with 10% methanol/dichloromethane (25 mL×3), the combined organic phase was washed with saturated salt water (25 mL×3), dried over anhydrous Na$_2$SO$_4$, and the solvent was distilled off under reduced pressure. The residue was then chromatographed (silica gel column chromatography, eluent: methanol:ethyl acetate=1:2) to give 0.768 g (2.21 mmol) of N-{1-[2-(1-methylpyrrolidin-2-yl)ethylamino]-1-oxoprop-2-yl}-5-formyl-2,4-dimethyl-1H-pyrrole-3-formamide. Yield 55.2%. $^1$HNMR (DMSO-d6) δ 10.83 (s, br, 1H, NH), 9.75 (s, 1H), 7.78 (m, br, 1H, CONHCH$_2$), 7.77 (m, br, 1H, CONHCH$_2$), 4.71 (m, 1H), 3.12-3.10 (m, 2H), 2.86 (m, 1H), 2.37-2.31 (m, 3H), 2.30-2.22 (m, 2H), 2.26-2.20 (s, 3H), 2.12-2.08 (m, 3H), 1.68-1.64 (m, 2H), 1.61-1.53 (m, 2H), 1.56-1.54 (m, 2H), 1.48-1.41 (d, 3H).

Example 21

Synthesis of N-[4-(dimethylamino)phenyl]-5-(5-fluoro-2-oxo-1,2-dihydroindole-3-methylene)-2,4-dimethyl-1H-pyrrole-3-formamide (Compound 7)

N-[4-(dimethylamino)phenyl]-5-formyl-2,4-dimethyl-1H-pyrrole-3-formamide (2.84 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 2.52 g (6.02 mmol) of N-[4-(dimethylamino) phenyl]-5-(5-fluoro-2-oxo-1,2-dihydroindole-3-methylene)-2,4-dimethyl-1H-pyrrole-3-formamide as a saffron solid. Yield 60.2%. $^1$HNMR (DMSO-d6) δ 13.65 (s, br, 1H, NH), 10.92 (s, br, 1H, NH), 9.34 (s, br, 1H, NH), 7.71 (s, 1H), 7.54-7.52 (d, 2H), 6.81-6.92 (m, 3H), 6.77-6.74 (d, 2H), 3.38-2.58 (s, 6H), 2.58-2.56 (m, 3H), 2.55-2.41 (m, 3H).

Example 22

Synthesis of N-{2-[4-(dimethylamino) anilino]-2-oxoethyl}-5-(5-fluoro-2-oxo-1,2-dihydroindole-3-methylene)-2,4-dimethyl-1H-pyrrole-3-formamide (Compound 8)

N-{2-[4-(dimethylamino)anilino]-2-oxoethyl}-5-formyl-2,4-dimethyl-1H-pyrrole-3-forma mide (3.41 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 3.11 g (6.55 mmol) of N-{2-[4-(dimethylamino)anilino]-2-oxoethyl}-5-(5-fluoro-2-oxo-1,2-dihydroindole-3-methylene)-2,4-dimethyl-1H-pyrrole-3-formamide as a saffron solid, yield 65.5%. $^1$HNMR (DMSO-d6) δ13.65 (s, br, 1H, NH), 10.83 (s, br, 1H, NH), 9.34 (s, br, 1H, NH), 7.71 (s, 1H), 7.65 (m, br, 1H, CONHCH$_2$), 7.54-7.52 (d, 2H), 6.81-6.92 (m, 3H), 6.77-6.74 (d, 2H), 3.81-3.73 (d, 2H), 3.38-2.58 (s, 6H), 2.58-2.56 (m, 3H), 2.55-2.41 (m, 3H).

Example 23

Synthesis of N-{1-[4-(dimethylamino) anilino]-1-oxoprop-2-yl}-5-(5-fluoro-2-oxo-1,2-dihydroindole-3-methylene)-2,4-dimethyl-1H-pyrrole-3-formamide (Compound 9)

N-{1-[4-(dimethylamino)anilino]-1-oxoprop-2-yl}-5-formyl-2,4-dimethyl-1H-pyrrole-3-formamide (3.56 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 3.44 g (7.03 mmol) of N-{1-[4-(dimethylamino)anilino]-1-oxoprop-2-y}-5-(5-fluoro-2-oxo-1,2-dihydroindole-3-methylene)-2,4-dimethyl-1H-pyrrole-3 formamide as a saffron solid. Yield 70.3%. $^1$HNMR (DMSO-d6) δ13.65 (s, br, 1H, NH), 10.83 (s, br, 1H, NH), 9.34 (s, br, 1H, NH), 7.71 (s, 1H), 7.65 (m, br, 1H, CONHCH$_2$), 7.54-7.52 (d, 2H), 6.81-6.92 (m, 3H), 6.77-6.74 (d, 2H), 4.71 (m, 1H), 3.38-2.58 (s, 6H), 2.58-2.56 (m, 3H), 2.55-2.41 (m, 3H), 1.48-1.41 (d, 3H).

Example 24

Synthesis of N-{2-[2-(diethylamino)ethylamino]-2-oxoethyl}-5-(5-fluoro-2-oxo-1,2-dihydroindole-3-methylene)-2,4-dimethyl-1H-pyrrole-3-formamide (Compound 10)

N-{2-[2-(diethylamino)ethylamino]-2-oxoethyl}-5-formyl-2,4-dimethyl-1H-pyrrole-3-form amide (3.22 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 3.74 g (8.22 mmol) of N-{2-[2-(diethylamino)ethylamino]-2-oxoethyl}-5-(5-fluoro-2-oxo-1,2-dihydroindole-3-methylene)-2,4-dimethyl-1H-pyrrole-3-formamide as a saffron solid. Yield 82.2%. $^1$HNMR (DMSO-d6) δ13.65 (s, br, 1H, NH), 10.83 (s, br, 1H, NH), 7.71 (s, 1H), 7.65 (m, br, 1H, CONHCH$_2$), 7.64 (m, br, 1H, CONHCH$_2$), 6.81-6.92 (m, 3H), 3.81-3.73 (d, 2H), 3.14-3.10 (m, 2H), 2.57-2.55 (m, 2H), 2.46-2.40 (m, 4H), 2.26-2.20 (s, 3H), 2.12-2.08 (m, 3H), 1.06-1.01 (m, 6H).

Example 25

Synthesis of N-{2-[(1-ethylpyrrolidin-2-yl)methylamino]-2-oxoethyl}-5-(5-fluoro-2-oxo-1,2-dihydroindole-3-methylene)-2,4-dimethyl-1H-pyrrole-3-formamide (Compound 11)

N-{2-[(1-ethylpyrrolidin-2-yl)methylamino]-2-oxoethyl}-5-formyl-2,4-dimethyl-1H-pyrrole-3-formamide (3.34 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 2.70 g (5.78 mmol) of N-{2-[(1-ethylpyrrolidin-2-yl)methylamino]-2-oxoethyl}-5-(5-fluoro-2-oxo-1,2-dihydroindole-3-methylene)-2,4-dimethyl-1H-pyrrole-3-formamide as a saffron solid. Yield 57.8%. $^1$HNMR (DMSO-d6) δ 13.65 (s, br, 1H, NH), 10.83 (s, br, 1H, NH), 7.74 (m, br, 1H, CONHCH$_2$), 7.73 (m, br, 1H, CONHCH$_2$), 7.71 (s, 1H), 6.81-6.92 (m, 3H), 3.85-3.83 (d, 2H), 3.07-3.03 (m, 2H), 2.85 (m, 1H), 2.49-2.46 (m, 2H), 2.32-2.30 (m, 2H), 2.23-2.20 (m, 3H), 2.12-2.08 (m, 3H), 1.68-1.64 (m, 2H), 1.56-1.54 (m, 2H), 1.06-1.01 (m, 3H).

Example 26

Synthesis of N-{2-[(1-ethylpyrrolidin-2-yl)methylamino]-1-oxoprop-2-yl}-5-(5-fluoro-2-oxo-1,2-dihydroindole-3-methylene)-2,4-dimethyl-1H-pyrrole-3-formamide (Compound 12)

N-{2-[(1-ethylpyrrolidin-2-yl)methylamino]-1-oxoprop-2-yl}-5-formyl-2,4-dimethyl-1H-pyrrole-3-formamide (3.48 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 2.73 g (5.86 mmol) of N-{2-{(1-ethylpyrrolidin-2-yl)methylamino]-1-oxoprop-2-yl}-5-(5-fluoro-2-oxo-1,2-dihydroindole-3-methylene)-2,4-dimethyl-1H-pyrrole-3-formamide as a saffron solid. Yield 58.6%. $^1$HNMR (DMSO-d6) δ 13.65 (s, br, 1H, NH), 10.83 (s, br, 1H, NH), 7.74 (m, br, 1H, CONHCH$_2$), 7.73 (m, br, 1H, CONHCH$_2$), 7.71 (s, 1H), 6.81-6.92 (m, 3H), 4.71 (m, 1H), 3.07-3.03 (m, 2H), 2.85 (m, 1H), 2.49-2.46 (m, 2H), 2.32-2.30 (m, 2H), 2.23-2.20 (m, 3H), 2.12-2.08 (m, 3H), 1.68-1.64 (m, 2H), 1.56-1.54 (m, 2H), 1.47-1.41 (d, 3H), 1.06-1.01 (m, 3H).

Example 27

Synthesis of N-{2-[2-(1-methylpyrrolidin-2-yl)ethylamino]-2-oxoethyl}-5-(5-fluoro-2-oxo-1,2-dihydroindole-3-methylene)-2,4-dimethyl-1H-pyrrole-3-formamide (Compound 13)

N-{2-[2-(1-methylpyrrolidin-2-yl)ethylamino]-2-oxoethyl}-5-formyl-2,4-dimethyl-1H-pyrrole-3-formamide (3.45 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 3.08 g (6.59 mmol) of N-{2-[2-(1-methylpyrrolidin-2-yl)ethylamino]-2-oxoethyl}-5-(5-fluoro-2-oxo-1,2-dihydroindole-3-methylene)-2,4-dimethyl-1H-pyrrole-3-formamide as a saffron solid. Yield 65.9%. $^1$HNMR (DMSO-d6) δ 13.69 (s, br, 1H, NH), 10.83 (s, br, 1H, NH), 7.74 (m, br, 1H, CONHCH$_2$), 7.73 (m, br, 1H, CONHCH$_2$), 7.71 (s, 1H), 6.81-6.92 (m, 3H), 3.85-3.83 (d, 2H), 3.12-3.10 (m, 2H), 2.86 (m, 1H), 2.37-2.31 (m, 3H), 2.30-2.22 (m, 2H), 2.23-2.20 (m, 3H), 2.12-2.08 (m, 3H), 1.68-1.64 (m, 2H), 1.61-1.53 (m, 2H), 1.56-1.54 (m, 2H).

Example 28

Synthesis of N-{1-[2-(1-methylpyrrolidin-2-yl)ethylamino]-1-oxoprop-2-yl}-5-(5-fluoro-2-oxo-1,2-dihydroindole-3-methylene)-2,4-dimethyl-1H-pyrrole-3-formamide (Compound 14)

N-{1-[2-(1-methylpyrrolidin-2-yl)ethylamino]-1-oxoprop-2-yl}-5-formyl-2,4-dimethyl-1H-pyrrole-3-formamide (3.48 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 2.29 g (4.77 mmol) of N-{1-[2-(1-methylpyrrolidin-2-yl)ethylamino]-1-oxoprop-2-yl}-5-(5-fluoro-2-oxo-1,2-dihydroindole-3-methylene)-2,4-dimethyl-1H-pyrrole-3-formamide as a saffron solid. Yield 47.7%. $^1$HNMR (DMSO-d6) δ 13.68 (s, br, 1H, NH), 10.82 (s, br, 1H, NH), 7.74 (m, br, 1H, CONHCH$_2$), 7.73 (m, br, 1H, CONHCH$_2$), 7.71 (s, 1H), 6.81-6.92 (m, 3H), 4.71 (m, 1H), 3.12-3.10 (m, 2H), 2.86 (m, 1H), 2.37-2.31 (m, 3H), 2.30-2.22 (m, 2H), 2.23-2.20 (m, 3H), 2.12-2.08 (m, 3H), 1.68-1.64 (m, 2H), 1.61-1.53 (m, 2H), 1.56-1.54 (m, 2H), 1.48-1.41 (d, 3H).

Example 29

Synthesis of N-{2-[(1-benzylpyrrolidin-3-yl)amino]-2-oxoethyl}-5-formyl-2,4-dimethyl-1H-pyrrole-3-formamide 2-Chloroacetic chloride (4.5 g, 40 mmol) was added dropwise to a solution of 1-benzylpyrrolidine-3-amine (7.04 g, 40 mmol) in dichloromethane (50 mL) with stirring at about 0° C. Afterwards, the reaction was warmed to room temperature and stirred until completion was indicated by thin layer chromatography (TLC). The solvent was distilled off to give 9.85 g (39.08 mmol) of an oily residue. Yield 97.7%.

The oily residue obtained in the above step and aqueous ammonia (300 mL) were added to methanol solution (300 mL) and stirred at about 45° C. until completion was indicated by thin layer chromatography (TLC). The solvent was distilled off to give 7.85 g (33.69 mmol) of an oily residue. Yield 86.2%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were sequentially added to DMF (10 mL) with stirring at about 0° C. and stirred for 1.5 hrs, and the compound obtained in the above step (1.86 g, 8 mmol) was added. The reaction was stirred at room temperature until completion was indicated by thin layer chromatography (TLC). 1.2 mL of water and 1 mL of saturated salt water were added, and the mixture was extracted with 10% methanol/dichloromethane (25 mL×3), the combined organic phase was washed with saturated salt water (25 mL×3), dried over anhydrous $Na_2SO_4$, and the solvent was distilled off under reduced pressure. The residue was then chromatographed (silica gel column chromatography, eluent: methanol:ethyl acetate=1:2) to give 0.614 g (1.61 mmol) of N-{2-[(1-benzylpyrrolidin-3-yl)amino]-2-oxoethyl}-5-formyl-2,4-dimethyl-1H-pyrrole-3-formamide. Yield 40.2%. $^1$HNMR (DMSO-d6) δ10.81 (s, br, 1H, NH), 9.64 (s, 1H), 7.63 (m, br, 1H, CONHCH$_2$), 6.92 (t, br, 1H, NH), 6.83-6.86 (m, 5H, benzene ring hydrogen), 3.81-3.75 (d, 2H), 3.67-3.68 (m, 1H), 3.50-3.669 (m, 2H), 3.16-3.17 (m, 2H), 2.32 (s, 3H), 2.33 (s, 3H), 1.71-1.82 (m, 2H), 1.10-1.11 (m, 2H).

Example 30

Synthesis of N-{2-[(1-benzylpyrrolidin-3-yl)amino]-2-oxoethyl}-5-(5-fluoro-2-oxo-1,2-dihydroindole-3-methylene)-2,4-dimethyl-1H-pyrrole-3-formamide (Compound 15)

N-{2-[(1-benzylpyrrolidin-3-yl)amino]-2-oxoethyl}-5-formyl-2,4-dimethyl-1H-pyrrole-3-formamide (3.82 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 3.72 g (7.22 mmol) of N-{2-[(1-benzylpyrrolidin-3-yl)amino]-2-oxoethyl}-5-(5-fluoro-2-oxo-1,2-dihydroindole-3-methylene)-2,4-dimethyl-1H-pyrrole-3-formamide (Compound 15) as a saffron solid. Yield 72.2%. $^1$HNMR (DMSO-d6) δ13.64 (s, br, 1H, NH), 10.81 (s, br, 1H, NH), 7.68-7.74 (m, 3H, benzene ring hydrogen), 7.63 (m, br, 1H, CONHCH$_2$), 7.26 (s, 1H), 6.92 (t, br, 1H, NH), 6.83-6.86 (m, 5H, benzene ring hydrogen), 3.81-3.75 (d, 2H), 3.67-3.68 (m, 1H), 3.50-3.669 (m, 2H), 3.16-3.17 (m, 2H), 2.32 (s, 3H), 2.33 (s, 3H), 1.71-1.82 (m, 2H), 1.10-1.11 (m, 2H).

Example 31

Synthesis of N-{2-[(piperidin-2-yl)methylamino]-2-oxoethyl}-5-formyl-2,4-dimethyl-1H-pyrrole-3-formamide 2-Chloroacetic chloride (4.5 g, 40 mmol) was added dropwise to a solution of 2-aminomethylpiperidine (4.56 g, 40 mmol) in dichloromethane (50 mL) with stirring at about 0° C. Afterwards, the reaction was warmed to room temperature and stirred until completion was indicated by thin layer chromatography (TLC). The solvent was distilled off to give 7.02 g (36.96 mmol) of an oily residue. Yield 92.4%.

The oily residue obtained in the above step and aqueous ammonia (300 mL) were added to methanol solution (300 mL) and stirred at about 45° C. until thin layer chromatography (TLC). The solvent was distilled off to give 5.37 g (31.42 mmol) of an oily residue. Yield 85.0%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, and the compound obtained in the above step (1.37 g, 8 mmol) was added. The reaction was stirred at room temperature until completion was indicated by thin layer chromatography (TLC). 1.2 mL of water and 1 mL of saturated salt water were added, and the mixture was extracted with 10% methanol/dichloromethane (25 mL×3), the combined organic phase was washed with saturated salt water (25 mL×3), dried over anhydrous $Na_2SO_4$, and the solvent was distilled off under reduced pressure. The residue was then chromatographed (silica gel column chromatography, eluent: methanol:ethyl acetate=1:2) to give 7.99 g (2.50 mmol) of N-{2-[(piperidin-2-yl)methylamino]-2-oxoethyl}-5-formyl-2,4-dimethyl-1H-pyrrole-3-formamide. Yield 62.4%. $^1$HNMR (DMSO-d6) δ10.82 (s, br, 1H, NH), 7.71 (s, 1H), 7.67 (m, br, 1H, CONHCH$_2$), 7.49 (t, br, 1H, NH), 4.40 (s, br, 1H, NH), 3.81-3.73 (d, 2H), 3.39-3.43 (m, 1H), 3.16-3.18 (m, 2H), 2.50 (s, 3H), 2.60 (s, 3H), 2.08-2.11 (m, 2H), 1.82-1.86 (m, 2H), 1.58-1.64 (m, 2H), 1.39-1.44 (m, 2H).

Example 32

Synthesis of N-{2-[(piperidin-2-yl)methylamino]-2-oxoethyl}-5-(5-fluoro-2-oxo-1,2-dihydroindole-3-methylene)-2,4-dimethyl-1H-pyrrole-3-formamide (Compound 16)

N-{2-[(piperidin-2-yl)methylamino]-2-oxoethyl}-5-formyl-2,4-dimethyl-1H-pyrrole-3-form amide (3.2 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 2.95 g (6.52 mmol) of N-{2-[(piperidin-2-yl)methylamino]-2-oxoethyl}-5-(5-fluoro-2-oxo-1,2-dihydroindole-3-methylene)-2,4-dimethyl-1H-pyrrole-3-formamide (Compound 16) as a saffron solid. Yield 65.2%. $^1$HNMR (DMSO-d6) δ13.67 (s, br, 1H, NH), 10.82 (s, br, 1H, NH), 7.74 (s, 1H, methene), 7.67 (m, br, 1H, CONHCH$_2$), 7.49 (t, br, 1H, NH), 6.83-6.94 (m, 3H, benzene ring hydrogen), 4.40 (s, br, 1H, NH), 3.81-3.73 (d, 2H), 3.39-3.43 (m, 1H), 3.16-3.18 (m, 2H), 2.50 (s, 3H), 2.60 (s, 3H), 2.08-2.11 (m, 2H), 1.82-1.86 (m, 2H), 1.58-1.64 (m, 2H), 1.39-1.44 (m, 2H).

Example 33

Synthesis of N-{2-[(piperidin-4-yl)methylamino]-2-oxoethyl}-5-formyl-2,4-dimethyl-1H-pyrrole-3-formamide 2-Chloroacetic chloride (4.5 g, 40 mmol) was added drop by drop to a solution of 4-aminomethylpiperidine (4.56 g, 40 mmol) in dichloromethane (50 mL) with stirring at about 0° C. Afterwards, the reaction was warmed to room temperature and stirred until completion was indicated by thin layer chromatography (TLC). The solvent was distilled off to give 6.74 g (35.68 mmol) of an oily residue. Yield 89.2%.

The oily residue obtained in the above step and aqueous ammonia (300 mL) were added to methanol solution (300 mL) and stirred at about 45° C. until completion was indicated by thin layer chromatography (TLC). The solvent was distilled off to give 5.04 g (29.47 mmol) of an oily residue. Yield 82.6%.

1-Ethyl-(3-dimethylaminopropyl) carbodiimide hydrochloride (1.074 g, 5.6 mmol), triethylamine (1.12 mL, 8 mmol), 5-formyl-2,4-dimethyl-1H-pyrrole-3-formic acid (0.668 g, 4 mmol) and 1-hydroxybenzotriazole (0.756 g, 5.6 mmol) were added to DMF (10 mL) with stirring at about 0° C. and stirred for 1.5 hrs, and the compound obtained in the above step (1.37 g, 8 mmol) was added. The reaction was stirred at room temperature until completion was indicated by thin layer chromatography (TLC). 1.2 mL of water and 1 mL of saturated salt water were added, and the mixture was extracted with 10% methanol/dichloromethane (25 mL×3), the combined organic phase was washed with saturated salt water (25 mL×3), dried over anhydrous $Na_2SO_4$, and the solvent was distilled off under reduced pressure. The residue was then chromatographed (silica gel column chromatography, eluent: methanol:ethyl acetate=1:2) to give 0.682 g (2.13 mmol) of N-{2-[(piperidin-4-yl)methylamino]-2-oxoethyl}-5-formyl-2,4-dimethyl-1H-pyrrole-3-formamide. Yield 53.3%. $^1$HNMR (DMSO-d6) δ10.82 (s, br, 1H, NH), 7.65 (m, br, 1H, $CONHCH_2$), 7.62 (t, br, 1H, NH), 7.58 (m, br, 1H, $CONHCH_2$), 4.41 (s, br, 1H, NH), 3.85-3.80 (d, 2H), 3.67-3.68 (m, 1H), 3.50-3.66 (m, 2H), 3.16-3.17 (m, 2H), 3.02-3.09 (m, 2H), 2.50 (s, 3H), 2.60 (s, 3H), 1.71-1.82 (m, 2H), 1.10-1.11 (m, 2H).

Example 34

Synthesis of N-{2-[(piperidin-4-yl)methylamino]-2-oxoethyl}-5-(5-fluoro-2-oxo-1,2-dihydroindole-3-methylene)-2,4-dimethyl-1H-pyrrole-3-formamide (Compound 17)

N-{2-[(piperidin-4-yl)methylamino]-2-oxoethyl}-5-formyl-2,4-dimethyl-1H-pyrrole-3-form amide (3.2 g, 10 mmol), 5-fluoro-2-indolone (1.51 g, 10 mmol), ethanol (20 mL) and pyrrolidine (0.04 mL) were mixed and heated to 78° C. with stirring, and allowed to react at this temperature for 3 hrs, cooled to room temperature, filtered and the collected solid was recrystallized from ethanol, dried to give 3.18 g (7.02 mmol) of N-{2-[(piperidin-4-yl)methylamino]-2-oxoethyl}-5-(5-fluoro-2-oxo-1,2-dihydroindole-3-methylene)-2,4-dimethyl-1H-pyrrole-3-formamide (Compound 17) as a saffron solid. Yield 70.2%. $^1$HNMR (DMSO-d6) δ13.66 (s, br, 1H, NH), 10.82 (s, br, 1H, NH), 7.68-7.74 (m, 3H, benzene ring hydrogen), 7.65 (m, br, 1H, $CONHCH_2$), 7.62 (t, br, 1H, NH), 6.83 (s, 1H, methene hydrogen), 4.41 (s, br, 1H, NH), 3.85-3.80 (d, 2H), 3.67-3.68 (m, 1H), 3.50-3.66 (m, 2H), 3.16-3.17 (m, 2H), 3.02-3.09 (m, 2H), 2.50 (s, 3H), 2.60 (s, 3H), 1.71-1.82 (m, 2H), 1.10-1.11 (m, 2H).

Example 35

Anti-Tumor Activity Assay

These tests were carried out using conventional operations in the art. Specifically, the following materials and methods were employed:

1. Tested Compounds

Sunitinib, Compounds 1-3, paclitaxel

2. Cell Lines

Human cervical cancer cell Hela, human liver cancer cell SMMC-7721, human lung cancer cell A549, poorly differentiated human gastric adenocarcinoma cell BGC-823, human breast cancer cell MDA-MB-231.

Note: Hela, BGC-823, SMMC7721 are commonly used cell lines, A549, MDA-MB-231 are Sunitinib-sensitive cell lines.

3. Methods

To a bottle containing exponential growth phase cells in good condition, 0.25% trypsin solution was added. Digestion resulted in falling off of adherent cells and the cells were counted (0.5–1×10$^4$ cells/mL) and prepared into a cell suspension. The cell suspension was seeded in a 96-well plate with an amount of 100 μL/well, incubated in a $CO_2$ incubator for 24 hrs. 20 μL/well of tested compounds were added, followed by 804, of 10% serum medium, and incubated for 48 hrs. 20 μL/well of MTT (5 mg/mL) was added to the 96-well plate, and the cells were incubated for 4 hrs in the incubator. After removing the supernatant, 150 μL/well of DMSO was added, and the cells were shaked in a horizontal swing bed for 10 minutes. Optical density value (OD value) of each well was measured with an ELISA analyzer at 490 nm, and cell inhibition rate was calculated. The corresponding solvent was used as negative control, and paclitaxel was used as positive control.

$$\text{Cell inhibition rate \%} = \frac{OD \text{ of negative control gruop} - OD \text{ of tested compounds group}}{OD \text{ of negative control group}} \times 100\%$$

1) The criteria for evaluation of anti tumor activity (NCI)

The criteria for evaluating activity of a compound was shown in the following table.

TABLE 1

| Compound μg/mL | Cell inhibition rate % | Activity |
|---|---|---|
| 1 | >50 | Strong (***) |
| 10 | >50 | |
| 100 | >50 | |
| 1 | <50 | Medium (**) |
| 10 | >50 | |
| 100 | >50 | |
| 1 | <50 | Weak (*) |
| 10 | <50 | |
| 100 | >50 | |

4. Results

TABLE 2

Effects of tested compounds on tumor cell proliferation

| Sample Nos. | Final concentration μg/mL | Hela Inhibition rate | Activity | SMMC-7721 Inhibition rate | Activity | BGC-823 Inhibition rate | Activity | A549 Inhibition rate | Activity | MDA-MB-231 Inhibition rate | Activity |
|---|---|---|---|---|---|---|---|---|---|---|---|
| Sunitinib | 0.1 | −0.21 | ** | −38.82 | ** | 9.53 | ** | 7.29 | ** | 6.4 | ** |
|  | 1 | 24.73 |  | −12.35 |  | 19.17 |  | 29.06 |  | 28.9 |  |
|  | 10 | 99.15 |  | 72.47 |  | 88.78 |  | 98.71 |  | 90.2 |  |
| Compound 1 | 0.1 | 4.69 | ** | −21.18 | ** | 14.77 | ** | 18.59 | ** | −8.3 | ** |
|  | 1 | 32.48 |  | −0.47 |  | 20.01 |  | 31.06 |  | 6.9 |  |
|  | 10 | 97.44 |  | 88.47 |  | 93.88 |  | 99.29 |  | 92.2 |  |
| Compound 2 | 0.1 | −6.18 | ** | −6.59 | ** | 4.73 | ** | 0.59 | ** | −0.2 | ** |
|  | 1 | 24.66 |  | −10.82 |  | 20.25 |  | 29.94 |  | 16.5 |  |
|  | 10 | 97.16 |  | 74.82 |  | 76.21 |  | 100.00 |  | 71.6 |  |
| Compound 3 | 0.1 | −3.20 | *** | −18.59 | ** | −5.42 | ** | 11.94 | ** | −5.4 | ** |
|  | 1 | 50.82 |  | 4.00 |  | 17.02 |  | 22.71 |  | 0.5 |  |
|  | 10 | 98.01 |  | 62.12 |  | 78.81 |  | 94.18 |  | 88.6 |  |
| Paclitaxel | 0.1 | 79.67 | *** | −6.71 |  | 85.06 | *** | 20.14 |  | 5.9 |  |
|  | 1 | 78.11 |  | −6.59 |  | 86.59 |  | 23.79 |  | 4.9 |  |
|  | 10 | 72.71 |  |  |  |  |  |  |  | 29.5 |  |

Note:
The samples added to Hela cellls was freshly prepared with DMSO, and the samples added to other cells were prepared one week before, stored at −20° C. for one week prior to use. The storage concentration of samples was 10 mg/ml.

Example 36

Anti-Tumor Activity Assay

The activity assay of the compounds of the invention was carried out through common methods in the art. Commercially available Sunitinib was used as positive control, and lung cancer cell H460, colon cancer cell COLO205 and HT29, breast cancer cell A435 were used as exemplary tumor cells. The tested compounds were prepared by the methods disclosed in the Examples above.

1. Cell Lines
Lung cancer cell H460, colon cancer cell COLO205 and HT29, breast cancer cell A435.

2. Methods
2.1 Inhibition of Tumor Cell Proliferation In Vitro
The test was carried out with conventional operations in the art, and specifically, the following method was employed:

A certain amount (100 μL/well, 0.5–1×10$^4$ cells/mL) of lung cancer cell H460, colon cancer cell COLO205, and breast cancer cell A435, etc. in logarithmic growth phase were seeded in a 96-well plate, and incubated in an incubator for 24 hrs at 37° C. and 5% $CO_2$. Afterwards, tested compounds and positive control (20 μL/wells) were added, followed by 804 of 10% serum medium, and then the tumor cells were incubated for further 48 hrs at 37° C. and 5% $CO_2$. Afterwards, MTT (5 mg/mL) was added to the 96-well plates (20 μL/well), and the cells were incubated for another 4 h. After removing the supernatant, the cells were dissolved with DMSO (150 μL/well) and measured with a microplate reader at 490 nm.

2.2 Growth Inhibition of Human Cancer HT-29 Cells Transplanted in Nude Mice
A piece of tumor tissue in vigorous growth phase was obtained and cut into the size of about 1.5 mm$^3$, and subcutaneously inoculated into the right axillary region of nude mice aseptically. Diameters of transplanted tumors in nude mice were measured with a vernier caliper. After tumors grew to 100~300 mm$^3$, the animals were randomly divided into 6 groups: model control group, Sunitinib group (30 mg/kg), Compound 1 group (30 mg/kg), Compound 2 group (30 mg/kg), Compound 3 group (30 mg/kg), Compound 4 group (30 mg/kg). Compounds 1-4 and Sunitinib were continuously administered intragastrically at 0.1 ml/10 g for 21 days, once a day. Meanwhile, the negative control group was administered equivalent amount of sterile saline. The dynamic observation of antitumor effects of compounds 1-4 and Sunitinib was performed by measuring tumor diameters. The tumor volumes were measured 2-3 times a week, and the body weights of nude mice were weighed at the same time and recorded. The general behavior of nude mice was observed and recorded daily.

Detection indicators and calculation methods:
(1) Tumor volume (TV), calculated by the equation:

$$TV = \frac{1}{2} \times a \times b^2$$

wherein a, b represent length and width, respectively.
(2) Relative tumor volume (RTV), calculated by the equation:

$$RTV = TV_t/TV_0$$

wherein $TV_0$ represents the tumor volume at the beginning of administration in separated cages (ie. $d_0$), $TV_t$ represents the tumor volume of each measurement.
(3) Relative tumor proliferation rate T/C (%)
T/C % = (TRTV/CRTV) × 100%
TRTV: RTV of positive control group and each test compound group. CRTV: RTV of model control group.

3. Results
3.1 Inhibition of Cell Proliferation In Vitro

TABLE 3

Growth inhibition of H460, COLO205, A435 in vitro

| Samples | $IC_{50}$(μM) |  |  |
|---|---|---|---|
|  | H460 | COLO205 | A435 |
| Compound 1 | 0.061 | 0.078 | 0.063 |
| Compound 2 | 0.16 | 0.11 | 0.085 |
| Compound 3 | 0.14 | 0.11 | 0.068 |
| Compound 4 | 0.58 | 0.40 | 0.22 |
| Compound 6 | 0.33 | 0.22 | 0.087 |

TABLE 3-continued

Growth inhibition of H460, COLO205, A435 in vitro

| Samples | IC$_{50}$(μM) | | |
|---|---|---|---|
| | H460 | COLO205 | A435 |
| Compound 7 | 0.23 | 0.17 | 0.082 |
| Compound 8 | 0.17 | 0.16 | 0.091 |
| Compound 11 | 0.41 | 0.28 | 0.15 |
| Compound 12 | 0.44 | 0.31 | 0.16 |
| Sunitinib | 0.68 | 0.55 | 0.63 |

The above results indicate that all of the compounds of the invention show superior proliferation inhibition of tumor cells H460, COLO205, A435, etc., than the control drug Sunitinib in vitro.

3.2 Growth Inhibition of Human Cancer HT-29 Cells Transplanted in Nude Mice

The results are shown in table 4 and FIG. 1, and indicate that: tested compounds and Sunitinib, which were continuously administered intragastrically at 30 mg/kg, show strong growth inhibition of human colon cancer HT-29 cells transplanted in nude mice, and T/C (%) are 51.5, 10.1, 17.8, 15.0, and 41.0, respectively, in which compound 1 shows the strongest inhibition of tumor proliferation.

Fibroblast NIH/3T3 in logarithmic growth phase was seeded in a 96-well plate, by a certain number of cells (100 μL/well, 0.5–1×10$^4$ cells/mL). After incubating for 24 h, the screened samples (20 μl/well) were added (directly added after cell suspension was seeded in the plate), incubated for further 48 h at 37° C. and 5% CO$_2$. Afterwards, MTT (5 mg/mL) was added to the 96-well plate (20 μL/well). The cells were incubated for another 4 h, and then dissolved with DMSO (150 μL/well) and measured with a microplate reader at 490 nm. The inhibition rate and IC$_{50}$ were calculated.

3. Results

NIH/3T3 cell is an in vitro screening model recognized at home and abroad. The test observed the effects of the compounds of the invention on NIH/3T3 proliferation, and provided experimental evidences for their prevention and treatment of fibrosis associated diseases clinically.

The results indicate that: the test compounds show a dose dependent inhibition of NIH/3T3 cell proliferation. IC$_{50}$ values are shown in table 5. The experimental data reveals that the compounds of the invention have a therapy effect on fibrosis proliferation associated diseases.

TABLE 4

Therapeutic effects on human cancer HT-29 cells transplanted in nude mice

| Group | Dose mg/kg | Number Beginning | Number Finally | Body weight (g) d0 | Body weight (g) d21 | TV d0 | TV d21 | RTV | T/C (%) |
|---|---|---|---|---|---|---|---|---|---|
| Model control group | — | 8 | 8 | 19.9 ± 2.1 | 21.1 ± 1.2 | 198.0 ± 65.1 | 1671.3 ± 634.7 | 8.8 ± 4.0 | — |
| Sunitinib | 30 | 6 | 6 | 20.4 ± 2.0 | 21.0 ± 1.9 | 198.2 ± 62.4 | 911.8 ± 481.7 | 4.6 ± 1.5* | 51.5 |
| Compound 1 group | 30 | 6 | 6 | 20.2 ± 1.9 | 21.5 ± 1.3 | 194.7 ± 57.7 | 163.7 ± 33.6 | 0.9 ± 0.2** | 10.1 |
| Compound 2 group | 30 | 6 | 6 | 19.7 ± 1.7 | 19.7 ± 1.6 | 193.5 ± 61.9 | 342.9 ± 284.7 | 1.6 ± 0.9** | 17.8 |
| Compound 3 group | 30 | 6 | 6 | 20.6 ± 2.0 | 20.8 ± 2.3 | 196.7 ± 62.7 | 290.4 ± 238.4 | 1.3 ± 0.7** | 15.0 |
| Compound 4 group | 30 | 6 | 6 | 20.0 ± 2.2 | 20.3 ± 1.5 | 195.0 ± 67.4 | 791.7 ± 815.0 | 3.6 ± 3.2* | 41.0 | d0: time of administration in separate cages.
**P < 0.01,
*P < 0.05 compared to model control group.

Example 37

Inhibition of Fibroblast Proliferation

The method commonly used at present for studying fibroblast proliferation associated diseases, i.e., for studying tissue and organ fibrosis, is measuring effects of test compounds on NIH/3T3 cell proliferation (Gao Z. M., Wan K., Effect of inhibition of NIH/3T3 cell proliferation by Cantharidin on prevention and treatment of organ and tissue fibrosis. Chinese Journal of Clinical Rehabilitation, 2004 (2). Tao Y. Y., Wang X. L., Effects of Salvianolic Acid-B on TGF-β1/ERK Signaling Transduction in NIH/3T3 Fibroblast. Journal of Capital Medical University, 2007 (2)).

I. Cells
  Fibroblast NIH/3T3
2. Method
  The test was performed using conventional operations in the art. Specifically, the following method was employed:

TABLE 5

Inhibition of NIH/3T3 cell proliferation in vitro

| Test Compounds | IC$_{50}$(μM) |
|---|---|
| Compound 1 | 0.205 |
| Compound 2 | 0.536 |
| Compound 3 | 0.530 |
| Compound 4 | 1.185 |
| Compound 6 | 0.698 |
| Compound 7 | 0.505 |
| Compound 8 | 0.884 |

The invention claimed is:

1. A compound of Formula I or a pharmaceutically acceptable salt thereof:

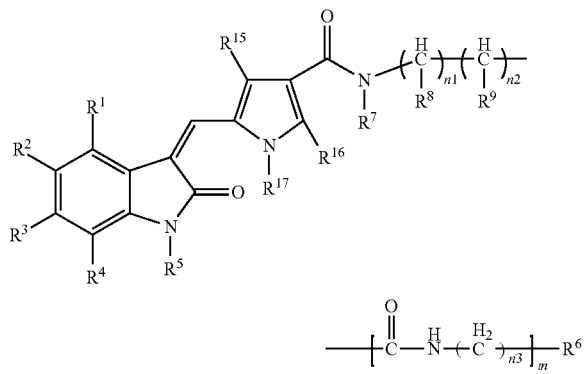

Formula I wherein:

R¹, R³ and R⁴ are each independently hydrogen;

R² is selected from the group consisting of hydrogen and halogen;

R⁵, R⁷ and R¹⁷ are each independently hydrogen;

R⁶ is selected from the group consisting of phenyl, phenyl substituted with di-$C_{1-8}$alkylamino, and a 5- or 6-membered heterocycloalkyl having one nitrogen as a heteroatom, optionally substituted with $C_{1-8}$ alkyl or phenyl-$C_{1-8}$ alkyl, with the proviso that when R⁶ is heterocycloalkyl, the heteroatom in R⁶ is not connected to other groups in Formula I directly;

R⁸ and R⁹ may be the same or different, and are each independently selected from the group consisting of hydrogen and $C_{1-8}$alkyl;

R¹⁵ and R¹⁶ may be the same or different, and are each independently $C_{1-8}$alkyl;

n1, n2 and n3 are each independently an integer from 0 to 4; and m is an integer from 0 to 2;

with the proviso that when R² is F, R¹⁵ and R¹⁶ are methyl group, R⁸ and R⁹ are hydrogen, n1+n2=0 or 1 and m=0, and R⁶ can not be a piperidin-4-yl optionally substituted with $C_1$-$C_2$ alkyl.

2. The compound of claim 1, wherein R¹, R³ and R⁴ are each independently hydrogen; R² is selected from the group consisting of hydrogen and halogen; R⁵, R⁷ and R¹⁷ are each independently hydrogen; R⁶ is selected from the group consisting of phenyl, phenyl substituted with di-$C_{1-8}$alkylamino, a 5- or 6-membered heterocycloalkyl having one nitrogen as a heteroatom, optionally substituted with $C_{1-8}$ alkyl, phenyl-$C_{1-8}$ alkyl, with the proviso that when R⁶ is heterocycloalkyl, the heteroatom in R⁶ is not connected to other groups in Formula I directly; R⁸ and R⁹ are each independently selected from the group consisting of hydrogen and $C_1$-$C_4$ alkyl; and R¹⁵ and R¹⁶ are each independently $C_1$-$C_4$ alkyl.

3. The compound of claim 1, which is selected from a compound of Formula II or a pharmaceutically acceptable salt thereof:

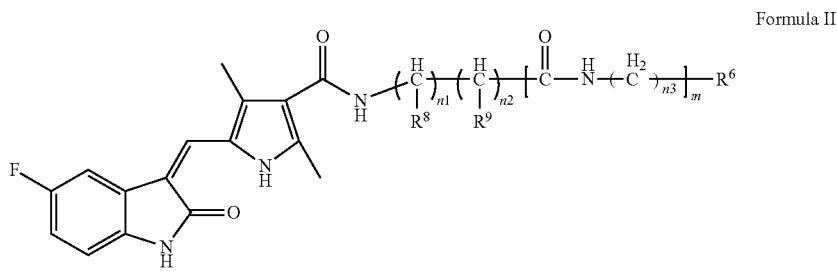

Formula II wherein R⁶, R⁸, R⁹, n1, n2 and n3 and m have the same meanings as defined in the compound of Formula I of claim 1.

4. The compound of claim 3, wherein R⁶ is selected from the group consisting of phenyl, phenyl substituted with di-$C_{1-8}$alkylamino, a 5- or 6-membered heterocycloalkyl having one nitrogen as a heteroatom, optionally substituted with $C_{1-8}$alkyl, phenyl-$C_{1-8}$ alkyl, with the proviso that when R⁶ is heterocycloalkyl, the heteroatom in R⁶ is not connected to other groups in Formula II directly; R⁸ and R⁹ are each independently selected from the group consisting of hydrogen and $C_1$-$C_4$ alkyl; n1, n2 and n3 are each independently an integer from 0 to 2, and m is an integer from 0 to 1.

5. A compound or a salt thereof selected from the group consisting of:

| No. | Structure | Name |
|---|---|---|
| 1 | 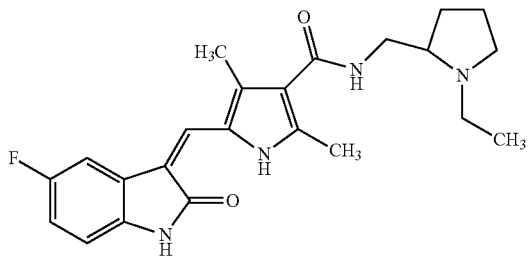 [SMILES: CCN1CCCC1CNC(=O)c1c(C)[nH]c(/C=C2\C(=O)Nc3ccc(F)cc32)c1C] | N-[(1-ethylpyrrolidin-2-yl)methyl]-5-(5-fluoro-2-oxo-1,2-dihydroindole-3-methylene)-2,4-dimethyl-1H-pyrrole-3-formamide |
| 2 | 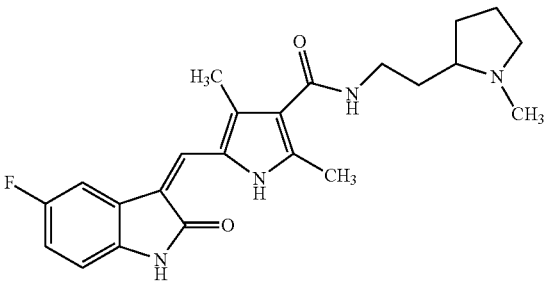 [SMILES: Cc1[nH]c(/C=C2\C(=O)Nc3ccc(F)cc32)c(C)c1C(=O)NCCC1CCCN1C] | N-[(1-methylpyrrolidin-2-yl)ethyl]-5-(5-fluoro-2-oxo-1,2-dihydroindole-3-methylene)-2,4-dimethyl-1H-pyrrole-3-formamide |
| 3 | 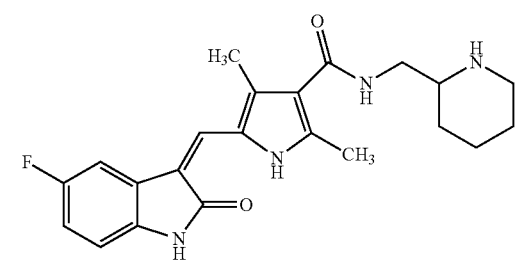 [SMILES: Cc1[nH]c(/C=C2\C(=O)Nc3ccc(F)cc32)c(C)c1C(=O)NCC1CCCCN1] | N-[(piperidin-2-yl)methyl-5-(5-fluoro-2-oxo-1,2-dihydroindole-3-methylene)-2,4-dimethyl-1H-pyrrole-3-formamide |
| 4 | 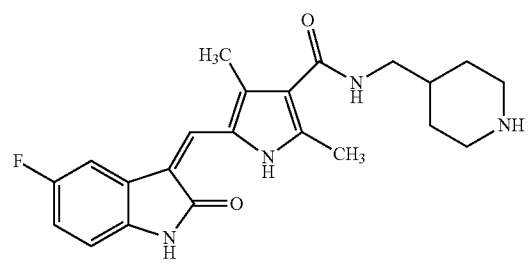 [SMILES: Cc1[nH]c(/C=C2\C(=O)Nc3ccc(F)cc32)c(C)c1C(=O)NCC1CCNCC1] | N-[(piperidin-4-yl)methyl-5-(5-fluoro-2-oxo-1,2-dihydroindole-3-methylene)-2,4-dimethyl-1H-pyrrole-3-formamide |
| 5 | 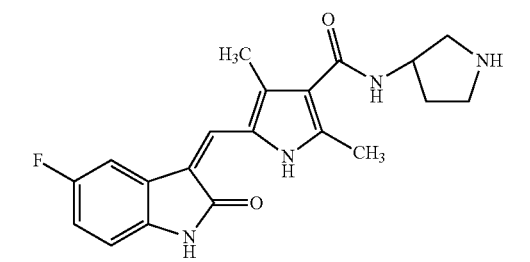 [SMILES: Cc1[nH]c(/C=C2\C(=O)Nc3ccc(F)cc32)c(C)c1C(=O)NC1CCNC1] | N-(pyrrolidin-3-yl)-5-(5-fluoro-2-oxo-1,2-dihydroindole-3-methylene)-2,4-dimethyl-1H-pyrrole-3-formamide |
| 6 | 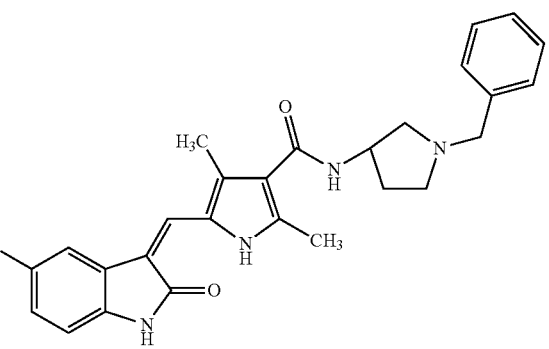 | N-(1-benzylpyrrolidin-3-yl)-5-(5-fluoro-2-oxo-1,2-dihydroindole-3-methylene)-2,4-dimethyl-1H-pyrrole-3-formamide |

6. A method for preparing the compound of claim 1, comprising reacting an intermediate of Formula III with an intermediate of Formula IV:

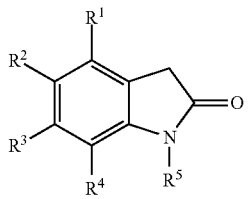

Formula III

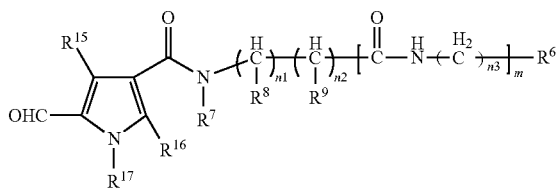

Formula IV wherein $R^1\sim R^9$, $R^{15}\sim R^{17}$, n1, n2, n3 and m have the same meanings as defined in Formula I of claim 1.

7. A method for preparing the compound of claim 3, comprising reacting an intermediate of Formula V with an intermediate of Formula VI:

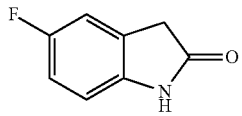

Formula V

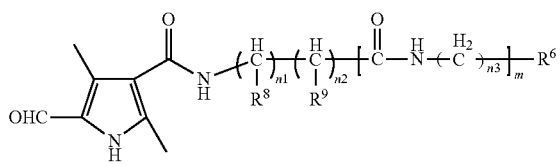

Formula VI wherein $R^6$, $R^8$, $R^9$, n1, n2, n3 and m have the same meanings as defined in Formula II of claim 3.

8. A pharmaceutical composition comprising the compound of claim 1, and one or more pharmaceutically acceptable carriers, excipients and/or vehicles.

9. A method for treating cervical carcinoma, liver cancer, lung cancer, gastric cancer, breast cancer or colon cancer, comprising administering to a subject in need thereof a therapeutically effective amount of the compound of claim 1.

10. A method for treating a fibroblast proliferation associated disease by inhibiting fibroblast proliferation in a subject in need thereof, comprising administering to the subject a therapeutically effective amount of the compound of claim 1, wherein the fibroblast proliferation associated disease is selected from the group consisting of hepatic fibrosis, chronic pancreatitis, scleroderma, renal glomerular fibrosis and multiple organ fibrosis supervened with radiochemotherapy and tissue transplantation.

11. The compound of claim 1, wherein n1, n2 and n3 are each independently selected from 0, 1 or 2; and m is selected from 0 or 1.

12. The compound of claim 1, wherein $R^6$ is phenyl substituted with di-$C_{1-8}$alkylamino.

13. The compound of claim 1, wherein $R^6$ is piperidin-2-yl, piperidin-4-yl, pyrrolidin-3-yl or pyrrolidin-2-yl that may be optionally substituted with $C_{1-4}$alkyl or phenyl-$C_{1-8}$alkyl.

* * * * *